US012533531B2

(12) United States Patent
Huston et al.

(10) Patent No.: US 12,533,531 B2
(45) Date of Patent: Jan. 27, 2026

(54) TREATING BLEEDING AND BLEEDING DISORDERS VIA HIGH INTENSITY FOCUSED ULTRASOUND STIMULATION OF THE SPLEEN

(71) Applicant: THE FEINSTEIN INSTITUTES FOR MEDICAL RESEARCH, Manhasset, NY (US)

(72) Inventors: Jared M. Huston, New York, NY (US); Jason R. Fritz, New York, NY (US); Catherine W. Imossi, Manhasset, NY (US); Kevin J. Tracey, Old Greenwich, CT (US)

(73) Assignee: The Feinstein Institutes for Medical Research, Manhasset, NY (US)

( * ) Notice: Subject to any disclaimer, the term of this patent is extended or adjusted under 35 U.S.C. 154(b) by 100 days.

(21) Appl. No.: 17/784,805

(22) PCT Filed: Jan. 13, 2021

(86) PCT No.: PCT/US2021/013190

§ 371 (c)(1),
(2) Date: Jun. 13, 2022

(87) PCT Pub. No.: WO2021/146247

PCT Pub. Date: Jul. 22, 2021

(65) Prior Publication Data

US 2023/0019961 A1 Jan. 19, 2023

Related U.S. Application Data

(60) Provisional application No. 62/960,612, filed on Jan. 13, 2020.

(51) Int. Cl.
*A61N 7/00* (2006.01)

(52) U.S. Cl.
CPC .................................... *A61N 7/00* (2013.01)

(58) Field of Classification Search
CPC ...................................................... A61N 7/00
See application file for complete search history.

(56) References Cited

U.S. PATENT DOCUMENTS 2,164,121 A 6/1939 Pescador
3,363,623 A 1/1968 Atwell
(Continued)

FOREIGN PATENT DOCUMENTS

CN 201230913 A 5/2009
CN 101528303 A 9/2009
(Continued)

OTHER PUBLICATIONS

US 6,184,239 B1, 02/2001, Puskas (withdrawn)
(Continued)

*Primary Examiner* — Hien N Nguyen
(74) *Attorney, Agent, or Firm* — Shay Glenn LLP

(57) ABSTRACT

Apparatuses and methods for reducing or limiting bleeding in an animal by focused ultrasound (FUS) stimulation of the spleen. The apparatuses and methods may be used treat blood disorders such as hemophilia, or to reduce hemorrhage in surgery or due to traumatic injury. The methods may be non-invasively administered to the patient by transcutaneous application of ultrasound energy.

18 Claims, 5 Drawing Sheets

(56) References Cited

U.S. PATENT DOCUMENTS

| | | | |
|---|---|---|---|
| 3,631,534 | A | 12/1971 | Hirota et al. |
| 4,073,296 | A | 2/1978 | McCall |
| 4,098,277 | A | 7/1978 | Mendell |
| 4,305,402 | A | 12/1981 | Katims |
| 4,503,863 | A | 3/1985 | Katims |
| 4,573,481 | A | 3/1986 | Bullara |
| 4,590,946 | A | 5/1986 | Loeb |
| 4,632,095 | A | 12/1986 | Libin |
| 4,649,936 | A | 3/1987 | Ungar et al. |
| 4,702,254 | A | 10/1987 | Zabara |
| 4,840,793 | A | 6/1989 | Todd et al. |
| 4,867,164 | A | 9/1989 | Zabara |
| 4,929,734 | A | 5/1990 | Coughenour et al. |
| 4,930,516 | A | 6/1990 | Alfano et al. |
| 4,935,234 | A | 6/1990 | Todd, III et al. |
| 4,979,511 | A | 12/1990 | Terry, Jr. |
| 4,991,578 | A | 2/1991 | Cohen |
| 5,019,648 | A | 5/1991 | Schlossman et al. |
| 5,025,807 | A | 6/1991 | Zabara |
| 5,038,781 | A | 8/1991 | Lynch |
| 5,049,659 | A | 9/1991 | Cantor et al. |
| 5,073,560 | A | 12/1991 | Wu et al. |
| 5,106,853 | A | 4/1992 | Showell et al. |
| 5,111,815 | A | 5/1992 | Mower |
| 5,154,172 | A | 10/1992 | Terry, Jr. et al. |
| 5,175,166 | A | 12/1992 | Dunbar et al. |
| 5,179,950 | A | 1/1993 | Stanislaw |
| 5,186,170 | A | 2/1993 | Varrichio et al. |
| 5,188,104 | A | 2/1993 | Wernicke et al. |
| 5,203,326 | A | 4/1993 | Collins |
| 5,205,285 | A | 4/1993 | Baker, Jr. |
| 5,215,086 | A | 6/1993 | Terry, Jr. et al. |
| 5,215,089 | A | 6/1993 | Baker, Jr. |
| 5,222,494 | A | 6/1993 | Baker, Jr. |
| 5,231,988 | A | 8/1993 | Wernicke et al. |
| 5,235,980 | A | 8/1993 | Varrichio et al. |
| 5,237,991 | A | 8/1993 | Baker et al. |
| 5,251,634 | A | 10/1993 | Weinberg |
| 5,263,480 | A | 11/1993 | Wernicke et al. |
| 5,269,303 | A | 12/1993 | Wernicke et al. |
| 5,299,569 | A | 4/1994 | Wernicke et al. |
| 5,304,206 | A | 4/1994 | Baker, Jr. et al. |
| 5,330,507 | A | 7/1994 | Schwartz |
| 5,330,515 | A | 7/1994 | Rutecki et al. |
| 5,335,657 | A | 8/1994 | Terry, Jr. et al. |
| 5,344,438 | A | 9/1994 | Testerman et al. |
| 5,351,394 | A | 10/1994 | Weinberg |
| 5,403,845 | A | 4/1995 | Dunbar et al. |
| 5,458,625 | A | 10/1995 | Kendall |
| 5,472,841 | A | 12/1995 | Jayasena et al. |
| 5,487,756 | A | 1/1996 | Kallesoe et al. |
| 5,496,938 | A | 3/1996 | Gold et al. |
| 5,503,978 | A | 4/1996 | Schneider et al. |
| 5,531,778 | A | 7/1996 | Maschino et al. |
| 5,540,730 | A | 7/1996 | Terry, Jr. et al. |
| 5,540,734 | A | 7/1996 | Zabara |
| 5,567,588 | A | 10/1996 | Gold et al. |
| 5,567,724 | A | 10/1996 | Kelleher et al. |
| 5,571,150 | A | 11/1996 | Wernicke et al. |
| 5,580,737 | A | 12/1996 | Polisky et al. |
| 5,582,981 | A | 12/1996 | Toole et al. |
| 5,604,231 | A | 2/1997 | Smith et al. |
| 5,607,459 | A | 3/1997 | Paul et al. |
| 5,611,350 | A | 3/1997 | John |
| 5,618,818 | A | 4/1997 | Ojo et al. |
| 5,629,285 | A | 5/1997 | Black et al. |
| 5,637,459 | A | 6/1997 | Burke et al. |
| 5,651,378 | A | 7/1997 | Matheny et al. |
| 5,654,151 | A | 8/1997 | Allen et al. |
| 5,683,867 | A | 11/1997 | Biesecker et al. |
| 5,690,681 | A | 11/1997 | Geddes et al. |
| 5,700,282 | A | 12/1997 | Zabara |
| 5,705,337 | A | 1/1998 | Gold et al. |
| 5,707,400 | A | 1/1998 | Terry, Jr. et al. |
| 5,709,853 | A | 1/1998 | Iino et al. |
| 5,712,375 | A | 1/1998 | Jensen et al. |
| 5,718,912 | A | 2/1998 | Thompson et al. |
| 5,726,017 | A | 3/1998 | Lochrie et al. |
| 5,726,179 | A | 3/1998 | Messer, Jr. et al. |
| 5,727,556 | A | 3/1998 | Weth et al. |
| 5,733,255 | A | 3/1998 | Dinh et al. |
| 5,741,802 | A | 4/1998 | Kem et al. |
| 5,773,598 | A | 6/1998 | Burke et al. |
| 5,786,462 | A | 7/1998 | Schneider et al. |
| 5,788,656 | A | 8/1998 | Mino |
| 5,792,210 | A | 8/1998 | Wamubu et al. |
| 5,824,027 | A | 10/1998 | Hoffer et al. |
| 5,853,005 | A | 12/1998 | Scanlon |
| 5,854,289 | A | 12/1998 | Bianchi et al. |
| 5,882,302 | A | 3/1999 | Driscoll, Jr. et al. |
| 5,902,814 | A | 5/1999 | Gordon et al. |
| 5,913,876 | A | 6/1999 | Taylor et al. |
| 5,916,239 | A | 6/1999 | Geddes et al. |
| 5,919,216 | A | 7/1999 | Houben et al. |
| 5,928,272 | A | 7/1999 | Adkins et al. |
| 5,964,794 | A | 10/1999 | Bolz et al. |
| 5,977,144 | A | 11/1999 | Meyer et al. |
| 5,994,330 | A | 11/1999 | El Khoury |
| 6,002,964 | A | 12/1999 | Feler et al. |
| 6,006,134 | A | 12/1999 | Hill et al. |
| 6,007,499 | A | 12/1999 | Martin et al. |
| 6,017,891 | A | 1/2000 | Eibl et al. |
| 6,028,186 | A | 2/2000 | Tasset et al. |
| 6,051,017 | A | 4/2000 | Loeb et al. |
| 6,083,696 | A | 7/2000 | Biesecker et al. |
| 6,083,905 | A | 7/2000 | Voorberg et al. |
| 6,096,728 | A | 8/2000 | Collins et al. |
| 6,104,956 | A | 8/2000 | Naritoku et al. |
| 6,110,900 | A | 8/2000 | Gold et al. |
| 6,110,914 | A | 8/2000 | Phillips et al. |
| 6,117,837 | A | 9/2000 | Tracey et al. |
| 6,124,449 | A | 9/2000 | Gold et al. |
| 6,127,119 | A | 10/2000 | Stephens et al. |
| 6,140,490 | A | 10/2000 | Biesecker et al. |
| 6,141,590 | A | 10/2000 | Renirie et al. |
| 6,147,204 | A | 11/2000 | Gold et al. |
| 6,159,145 | A | 12/2000 | Satoh |
| 6,164,284 | A | 12/2000 | Schulman et al. |
| 6,166,048 | A | 12/2000 | Bencherif |
| 6,168,778 | B1 | 1/2001 | Janjic et al. |
| 6,171,795 | B1 | 1/2001 | Korman et al. |
| 6,205,359 | B1 | 3/2001 | Boveja |
| 6,208,894 | B1 | 3/2001 | Schulman et al. |
| 6,208,902 | B1 | 3/2001 | Boveja |
| 6,210,321 | B1 | 4/2001 | Di Mino et al. |
| 6,224,862 | B1 | 5/2001 | Turecek et al. |
| 6,233,488 | B1 | 5/2001 | Hess |
| 6,266,564 | B1 | 7/2001 | Hill et al. |
| 6,269,270 | B1 | 7/2001 | Boveja |
| 6,304,775 | B1 | 10/2001 | Lasemidis et al. |
| 6,308,104 | B1 | 10/2001 | Taylor et al. |
| 6,337,997 | B1 | 1/2002 | Rise |
| 6,339,725 | B1 | 1/2002 | Naritoku et al. |
| 6,341,236 | B1 | 1/2002 | Osorio et al. |
| 6,356,787 | B1 | 3/2002 | Rezai et al. |
| 6,356,788 | B2 | 3/2002 | Boveja |
| 6,381,499 | B1 | 4/2002 | Taylor et al. |
| 6,405,732 | B1 | 6/2002 | Edwards et al. |
| 6,407,095 | B1 | 6/2002 | Lochead et al. |
| 6,428,484 | B1 | 8/2002 | Battmer et al. |
| 6,429,217 | B1 | 8/2002 | Puskas |
| 6,447,443 | B1 | 9/2002 | Keogh et al. |
| 6,449,507 | B1 | 9/2002 | Hill et al. |
| 6,473,644 | B1 | 10/2002 | Terry, Jr. et al. |
| 6,479,523 | B1 | 11/2002 | Puskas |
| 6,487,446 | B1 | 11/2002 | Hill et al. |
| 6,511,500 | B1 | 1/2003 | Rahme |
| 6,528,529 | B1 | 3/2003 | Brann et al. |
| 6,532,388 | B1 | 3/2003 | Hill et al. |
| 6,542,774 | B2 | 4/2003 | Hill et al. |
| 6,556,868 | B2 | 4/2003 | Naritoku et al. |
| 6,564,102 | B1 | 5/2003 | Boveja |
| 6,587,719 | B1 | 7/2003 | Barrett et al. |
| 6,587,727 | B2 | 7/2003 | Osorio et al. |

(56) References Cited

U.S. PATENT DOCUMENTS 6,600,956 B2 7/2003 Maschino et al.
6,602,891 B2 8/2003 Messer et al.
6,609,025 B2 8/2003 Barrett et al.
6,610,713 B2 8/2003 Tracey
6,611,715 B1 8/2003 Boveja
6,615,081 B1 9/2003 Boveja
6,615,085 B1 9/2003 Boveja
6,622,038 B2 9/2003 Barrett et al.
6,622,041 B2 9/2003 Terry, Jr. et al.
6,622,047 B2 9/2003 Barrett et al.
6,628,987 B1 9/2003 Hill et al.
6,633,779 B1 10/2003 Schuler et al.
6,656,960 B2 12/2003 Puskas
6,668,191 B1 12/2003 Boveja
6,671,556 B2 12/2003 Osorio et al.
6,684,105 B2 1/2004 Cohen et al.
6,690,973 B2 2/2004 Hill et al.
6,718,208 B2 4/2004 Hill et al.
6,721,603 B2 4/2004 Zabara et al.
6,735,471 B2 5/2004 Hill et al.
6,735,475 B1 5/2004 Whitehurst et al.
6,760,626 B1 7/2004 Boveja
6,778,854 B2 8/2004 Puskas
6,804,558 B2 10/2004 Haller et al.
RE38,654 E 11/2004 Hill et al.
6,826,428 B1 11/2004 Chen et al.
6,832,114 B1 12/2004 Whitehurst et al.
6,838,471 B2 1/2005 Tracey
RE38,705 E 2/2005 Hill et al.
6,879,859 B1 4/2005 Boveja
6,885,888 B2 4/2005 Rezai
6,901,294 B1 5/2005 Whitehurst et al.
6,904,318 B2 6/2005 Hill et al.
6,920,357 B2 7/2005 Osorio et al.
6,928,320 B2 8/2005 King
6,934,583 B2 8/2005 Weinberg et al.
6,937,903 B2 8/2005 Schuler et al.
6,961,618 B2 11/2005 Osorio et al.
6,978,787 B1 12/2005 Broniatowski
7,011,638 B2 3/2006 Schuler et al.
7,054,686 B2 5/2006 MacDonald
7,054,692 B1 5/2006 Whitehurst et al.
7,058,447 B2 6/2006 Hill et al.
7,062,320 B2 6/2006 Ehlinger, Jr.
7,069,082 B2 6/2006 Lindenthaler
7,072,720 B2 7/2006 Puskas
7,076,307 B2 7/2006 Boveja et al.
7,142,910 B2 11/2006 Puskas
7,142,917 B2 11/2006 Fukui
7,149,574 B2 12/2006 Yun et al.
7,155,279 B2 12/2006 Whitehurst et al.
7,155,284 B1 12/2006 Whitehurst et al.
7,167,750 B2 1/2007 Knudson et al.
7,167,751 B1 1/2007 Whitehurst et al.
7,174,218 B1 2/2007 Kuzma
7,184,828 B2 2/2007 Hill et al.
7,184,829 B2 2/2007 Hill et al.
7,191,012 B2 3/2007 Boveja et al.
7,204,815 B2 4/2007 Connor
7,209,787 B2 4/2007 DiLorenzo
7,225,019 B2 5/2007 Jahns et al.
7,228,167 B2 6/2007 Kara et al.
7,238,715 B2 7/2007 Tracey et al.
7,242,984 B2 7/2007 DiLorenzo
7,269,457 B2 9/2007 Shafer et al.
7,345,178 B2 3/2008 Nunes et al.
7,373,204 B2 5/2008 Gelfand et al.
7,389,145 B2 6/2008 Kilgore et al.
7,454,245 B2 11/2008 Armstrong et al.
7,467,016 B2 12/2008 Colborn
7,544,497 B2 6/2009 Sinclair et al.
7,561,918 B2 7/2009 Armstrong et al.
7,711,432 B2 5/2010 Thimineur et al.
7,729,760 B2 6/2010 Patel et al.
7,751,891 B2 7/2010 Armstrong et al.
7,776,326 B2 8/2010 Milbrandt et al.
7,797,058 B2 9/2010 Mrva et al.
7,819,883 B2 10/2010 Westlund et al.
7,822,486 B2 10/2010 Foster et al.
7,829,556 B2 11/2010 Bemis et al.
7,869,885 B2 1/2011 Begnaud et al.
7,937,145 B2 5/2011 Dobak
7,962,220 B2 6/2011 Kolafa et al.
7,974,701 B2 7/2011 Armstrong
7,974,707 B2 7/2011 Inman
7,996,088 B2 8/2011 Marrosu et al.
7,996,092 B2 8/2011 Mrva et al.
8,019,419 B1 9/2011 Panescu et al.
8,060,208 B2 11/2011 Kilgore et al.
8,103,349 B2 1/2012 Donders et al.
8,165,668 B2 4/2012 Dacey, Jr. et al.
8,180,446 B2 5/2012 Dacey, Jr. et al.
8,180,447 B2 5/2012 Dacey et al.
8,195,287 B2 6/2012 Dacey, Jr. et al.
8,214,056 B2 7/2012 Hoffer et al.
8,233,982 B2 7/2012 Libbus
8,391,970 B2 3/2013 Tracey et al.
8,412,338 B2 4/2013 Faltys
8,504,161 B1 8/2013 Kornet et al.
8,571,654 B2 10/2013 Libbus et al.
8,577,458 B1 11/2013 Libbus et al.
8,600,505 B2 12/2013 Libbus et al.
8,612,002 B2 12/2013 Faltys et al.
8,630,709 B2 1/2014 Libbus et al.
8,688,212 B2 4/2014 Libbus et al.
8,700,150 B2 4/2014 Libbus et al.
8,729,129 B2 5/2014 Tracey et al.
8,788,034 B2 7/2014 Levine et al.
8,843,210 B2 9/2014 Simon et al.
8,855,767 B2 10/2014 Faltys et al.
8,886,339 B2 11/2014 Faltys et al.
8,914,114 B2 12/2014 Tracey et al.
8,918,178 B2 12/2014 Simon et al.
8,918,191 B2 12/2014 Libbus et al.
8,923,964 B2 12/2014 Libbus et al.
8,983,628 B2 3/2015 Simon et al.
8,983,629 B2 3/2015 Simon et al.
8,996,116 B2 3/2015 Faltys et al.
9,114,262 B2 8/2015 Libbus et al.
9,162,064 B2 10/2015 Faltys et al.
9,174,041 B2 11/2015 Faltys et al.
9,211,409 B2 12/2015 Tracey et al.
9,211,410 B2 12/2015 Levine et al.
9,254,383 B2 2/2016 Simon et al.
9,272,143 B2 3/2016 Libbus et al.
9,358,381 B2 6/2016 Simon et al.
9,399,134 B2 7/2016 Simon et al.
9,403,001 B2 8/2016 Simon et al.
9,409,024 B2 8/2016 KenKnight et al.
9,415,224 B2 8/2016 Libbus et al.
9,452,290 B2 9/2016 Libbus et al.
9,504,832 B2 11/2016 Libbus et al.
9,511,228 B2 12/2016 Amurthur et al.
9,533,153 B2 1/2017 Libbus et al.
9,572,983 B2 2/2017 Levine et al.
9,662,490 B2 5/2017 Tracey et al.
9,700,716 B2 7/2017 Faltys et al.
9,833,621 B2 12/2017 Levine
9,849,286 B2 12/2017 Levine et al.
9,987,492 B2 6/2018 Tracey et al.
9,993,651 B2 6/2018 Faltys et al.
10,166,395 B2 1/2019 Tracey et al.
10,220,203 B2 3/2019 Faltys et al.
10,449,358 B2 10/2019 Levine et al.
10,561,846 B2 2/2020 Tracey et al.
10,583,304 B2 3/2020 Faltys et al.
10,596,367 B2 3/2020 Faltys et al.
10,695,569 B2 6/2020 Levine et al.
10,716,936 B2 7/2020 Faltys et al.
10,912,712 B2 2/2021 Tracey et al.
11,051,744 B2 7/2021 Levine et al.
11,110,287 B2 9/2021 Faltys et al.
11,173,307 B2 11/2021 Levine et al.
11,207,518 B2 12/2021 Huston et al.

(56) References Cited

U.S. PATENT DOCUMENTS

| | | | |
|---|---|---|---|
| 11,260,229 | B2 | 3/2022 | Manogue |
| 11,278,718 | B2 | 3/2022 | Faltys et al. |
| 11,311,725 | B2 | 4/2022 | Levine et al. |
| 11,344,724 | B2 | 5/2022 | Huston et al. |
| 11,383,091 | B2 | 7/2022 | Faltys et al. |
| 11,406,833 | B2 | 8/2022 | Faltys et al. |
| 2001/0002441 | A1 | 5/2001 | Boveja |
| 2001/0034542 | A1 | 10/2001 | Mann |
| 2002/0026141 | A1 | 2/2002 | Houben et al. |
| 2002/0040035 | A1 | 4/2002 | Myers et al. |
| 2002/0077675 | A1 | 6/2002 | Greenstein |
| 2002/0086871 | A1 | 7/2002 | O'Neill et al. |
| 2002/0095139 | A1 | 7/2002 | Keogh et al. |
| 2002/0099417 | A1 | 7/2002 | Naritoku et al. |
| 2002/0138075 | A1 | 9/2002 | Edwards et al. |
| 2002/0138109 | A1 | 9/2002 | Keogh et al. |
| 2002/0193859 | A1 | 12/2002 | Schulman et al. |
| 2002/0198570 | A1 | 12/2002 | Puskas |
| 2003/0018367 | A1 | 1/2003 | DiLorenzo |
| 2003/0032852 | A1 | 2/2003 | Perreault et al. |
| 2003/0045909 | A1 | 3/2003 | Gross et al. |
| 2003/0088301 | A1 | 5/2003 | King |
| 2003/0191404 | A1 | 10/2003 | Klein |
| 2003/0194752 | A1 | 10/2003 | Anderson et al. |
| 2003/0195578 | A1 | 10/2003 | Perron et al. |
| 2003/0212440 | A1 | 11/2003 | Boveja |
| 2003/0229380 | A1 | 12/2003 | Adams et al. |
| 2003/0236557 | A1 | 12/2003 | Whitehurst et al. |
| 2003/0236558 | A1 | 12/2003 | Whitehurst et al. |
| 2004/0002546 | A1 | 1/2004 | Altschuler |
| 2004/0015202 | A1 | 1/2004 | Chandler et al. |
| 2004/0015204 | A1 | 1/2004 | Whitehurst et al. |
| 2004/0015205 | A1 | 1/2004 | Whitehurst et al. |
| 2004/0024422 | A1 | 2/2004 | Hill et al. |
| 2004/0024428 | A1 | 2/2004 | Barrett et al. |
| 2004/0024439 | A1 | 2/2004 | Riso |
| 2004/0030362 | A1 | 2/2004 | Hill et al. |
| 2004/0039427 | A1 | 2/2004 | Barrett et al. |
| 2004/0048795 | A1 | 3/2004 | Ivanova et al. |
| 2004/0049121 | A1 | 3/2004 | Yaron |
| 2004/0049240 | A1 | 3/2004 | Gerber et al. |
| 2004/0059383 | A1 | 3/2004 | Puskas |
| 2004/0111139 | A1 | 6/2004 | McCreery et al. |
| 2004/0138517 | A1 | 7/2004 | Osorio et al. |
| 2004/0138518 | A1 | 7/2004 | Rise et al. |
| 2004/0138536 | A1 | 7/2004 | Frei et al. |
| 2004/0146949 | A1 | 7/2004 | Tan et al. |
| 2004/0153127 | A1 | 8/2004 | Gordon et al. |
| 2004/0158119 | A1 | 8/2004 | Osorio et al. |
| 2004/0162584 | A1 | 8/2004 | Hill et al. |
| 2004/0172074 | A1 | 9/2004 | Yoshihito |
| 2004/0172085 | A1 | 9/2004 | Knudson et al. |
| 2004/0172086 | A1 | 9/2004 | Knudson et al. |
| 2004/0172088 | A1 | 9/2004 | Knudson et al. |
| 2004/0172094 | A1 | 9/2004 | Cohen et al. |
| 2004/0176812 | A1 | 9/2004 | Knudson et al. |
| 2004/0178706 | A1 | 9/2004 | D'Orso |
| 2004/0193231 | A1 | 9/2004 | David et al. |
| 2004/0199209 | A1 | 10/2004 | Hill et al. |
| 2004/0199210 | A1 | 10/2004 | Shelchuk |
| 2004/0204355 | A1 | 10/2004 | Tracey et al. |
| 2004/0215272 | A1 | 10/2004 | Haubrich et al. |
| 2004/0215287 | A1 | 10/2004 | Swoyer et al. |
| 2004/0236381 | A1 | 11/2004 | Dinsmoor et al. |
| 2004/0236382 | A1 | 11/2004 | Dinsmoor et al. |
| 2004/0240691 | A1 | 12/2004 | Grafenberg |
| 2004/0243182 | A1 | 12/2004 | Cohen et al. |
| 2004/0254612 | A1 | 12/2004 | Ezra et al. |
| 2004/0267152 | A1 | 12/2004 | Pineda |
| 2005/0021092 | A1 | 1/2005 | Yun et al. |
| 2005/0021101 | A1 | 1/2005 | Chen et al. |
| 2005/0027328 | A1 | 2/2005 | Greenstein |
| 2005/0043774 | A1 | 2/2005 | Devlin et al. |
| 2005/0049655 | A1 | 3/2005 | Boveja et al. |
| 2005/0065553 | A1 | 3/2005 | Ben Ezra et al. |
| 2005/0065573 | A1 | 3/2005 | Rezai |
| 2005/0065575 | A1 | 3/2005 | Dobak |
| 2005/0070970 | A1 | 3/2005 | Knudson et al. |
| 2005/0070974 | A1 | 3/2005 | Knudson et al. |
| 2005/0075701 | A1 | 4/2005 | Shafer |
| 2005/0075702 | A1 | 4/2005 | Shafer |
| 2005/0095246 | A1 | 5/2005 | Shafer |
| 2005/0096707 | A1 | 5/2005 | Hill et al. |
| 2005/0103351 | A1 | 5/2005 | Stomberg et al. |
| 2005/0113894 | A1 | 5/2005 | Zilberman et al. |
| 2005/0131467 | A1 | 6/2005 | Boveja |
| 2005/0131486 | A1 | 6/2005 | Boveja et al. |
| 2005/0131487 | A1 | 6/2005 | Boveja |
| 2005/0131493 | A1 | 6/2005 | Boveja et al. |
| 2005/0137644 | A1 | 6/2005 | Boveja et al. |
| 2005/0137645 | A1 | 6/2005 | Voipio et al. |
| 2005/0143781 | A1 | 6/2005 | Carbunaru et al. |
| 2005/0143787 | A1 | 6/2005 | Boveja et al. |
| 2005/0149126 | A1 | 7/2005 | Libbus |
| 2005/0149129 | A1 | 7/2005 | Libbus et al. |
| 2005/0149131 | A1 | 7/2005 | Libbus et al. |
| 2005/0153885 | A1 | 7/2005 | Yun et al. |
| 2005/0154425 | A1 | 7/2005 | Boveja et al. |
| 2005/0154426 | A1 | 7/2005 | Boveja et al. |
| 2005/0165458 | A1 | 7/2005 | Boveja et al. |
| 2005/0177200 | A1 | 8/2005 | George et al. |
| 2005/0182288 | A1 | 8/2005 | Zabara |
| 2005/0182467 | A1 | 8/2005 | Hunter et al. |
| 2005/0187584 | A1 | 8/2005 | Denker et al. |
| 2005/0187586 | A1 | 8/2005 | David et al. |
| 2005/0187590 | A1 | 8/2005 | Boveja et al. |
| 2005/0191661 | A1 | 9/2005 | Gatanaga et al. |
| 2005/0192644 | A1 | 9/2005 | Boveja et al. |
| 2005/0197600 | A1 | 9/2005 | Schuler et al. |
| 2005/0197675 | A1 | 9/2005 | David et al. |
| 2005/0197678 | A1 | 9/2005 | Boveja et al. |
| 2005/0203501 | A1 | 9/2005 | Aldrich et al. |
| 2005/0209654 | A1 | 9/2005 | Boveja et al. |
| 2005/0216064 | A1 | 9/2005 | Heruth et al. |
| 2005/0216070 | A1 | 9/2005 | Boveja et al. |
| 2005/0216071 | A1 | 9/2005 | Devlin et al. |
| 2005/0240229 | A1 | 10/2005 | Whitehurst et al. |
| 2005/0240231 | A1 | 10/2005 | Aldrich et al. |
| 2005/0240241 | A1 | 10/2005 | Yun et al. |
| 2005/0240242 | A1 | 10/2005 | DiLorenzo |
| 2005/0251220 | A1 | 11/2005 | Barrett et al. |
| 2005/0251222 | A1 | 11/2005 | Barrett et al. |
| 2005/0267542 | A1 | 12/2005 | David et al. |
| 2005/0267547 | A1 | 12/2005 | Knudson et al. |
| 2005/0277912 | A1 | 12/2005 | John |
| 2005/0283198 | A1 | 12/2005 | Haubrich et al. |
| 2006/0009815 | A1 | 1/2006 | Boveja et al. |
| 2006/0015151 | A1 | 1/2006 | Aldrich |
| 2006/0025828 | A1 | 2/2006 | Armstrong et al. |
| 2006/0036293 | A1 | 2/2006 | Whitehurst et al. |
| 2006/0052657 | A9 | 3/2006 | Zabara |
| 2006/0052831 | A1 | 3/2006 | Fukui |
| 2006/0052836 | A1 | 3/2006 | Kim et al. |
| 2006/0058851 | A1 | 3/2006 | Cigaina |
| 2006/0064137 | A1 | 3/2006 | Stone |
| 2006/0064139 | A1 | 3/2006 | Chung et al. |
| 2006/0074450 | A1 | 4/2006 | Boveja et al. |
| 2006/0074473 | A1 | 4/2006 | Gertner |
| 2006/0079936 | A1 | 4/2006 | Boveja et al. |
| 2006/0085046 | A1 | 4/2006 | Rezai et al. |
| 2006/0095081 | A1 | 5/2006 | Zhou et al. |
| 2006/0095090 | A1 | 5/2006 | De Ridder |
| 2006/0100668 | A1 | 5/2006 | Ben-David et al. |
| 2006/0106755 | A1 | 5/2006 | Stuhec |
| 2006/0111644 | A1 | 5/2006 | Guttag et al. |
| 2006/0111754 | A1 | 5/2006 | Rezai et al. |
| 2006/0111755 | A1 | 5/2006 | Stone et al. |
| 2006/0116739 | A1 | 6/2006 | Betser et al. |
| 2006/0122675 | A1 | 6/2006 | Libbus et al. |
| 2006/0129200 | A1 | 6/2006 | Kurokawa |
| 2006/0129202 | A1 | 6/2006 | Armstrong |
| 2006/0135998 | A1 | 6/2006 | Libbus et al. |
| 2006/0136024 | A1 | 6/2006 | Cohen et al. |
| 2006/0142802 | A1 | 6/2006 | Armstrong |

(56) References Cited

U.S. PATENT DOCUMENTS

2006/0142822 A1 6/2006 Tulgar
2006/0149337 A1 7/2006 John
2006/0155495 A1 7/2006 Osorio et al.
2006/0161216 A1 7/2006 John et al.
2006/0161217 A1 7/2006 Jaax et al.
2006/0167497 A1 7/2006 Armstrong et al.
2006/0167498 A1 7/2006 DiLorenzo
2006/0167501 A1 7/2006 Ben-David et al.
2006/0173493 A1 8/2006 Armstrong et al.
2006/0173508 A1 8/2006 Stone et al.
2006/0178691 A1 8/2006 Binmoeller
2006/0178706 A1 8/2006 Lisogurski et al.
2006/0190044 A1 8/2006 Libbus et al.
2006/0200208 A1 9/2006 Terry, Jr. et al.
2006/0200219 A1 9/2006 Thrope et al.
2006/0206155 A1 9/2006 Ben-David et al.
2006/0206158 A1 9/2006 Wu et al.
2006/0229677 A1 10/2006 Moffitt et al.
2006/0229681 A1 10/2006 Fischell
2006/0241697 A1 10/2006 Libbus et al.
2006/0241699 A1 10/2006 Libbus et al.
2006/0247719 A1 11/2006 Maschino et al.
2006/0247721 A1 11/2006 Maschino et al.
2006/0247722 A1 11/2006 Maschino et al.
2006/0259077 A1 11/2006 Pardo et al.
2006/0259084 A1 11/2006 Zhang et al.
2006/0259085 A1 11/2006 Zhang et al.
2006/0259107 A1 11/2006 Caparso et al.
2006/0271115 A1 11/2006 Ben-Ezra et al.
2006/0282121 A1 12/2006 Payne et al.
2006/0282131 A1 12/2006 Caparso et al.
2006/0282145 A1 12/2006 Caparso et al.
2006/0287678 A1 12/2006 Shafer
2006/0287679 A1 12/2006 Stone
2006/0292099 A1 12/2006 Milburn et al.
2006/0293720 A1 12/2006 DiLorenzo
2006/0293721 A1 12/2006 Tarver et al.
2006/0293723 A1 12/2006 Whitehurst et al.
2007/0016262 A1 1/2007 Gross et al.
2007/0016263 A1 1/2007 Armstrong et al.
2007/0021785 A1 1/2007 Inman et al.
2007/0021786 A1 1/2007 Parnis et al.
2007/0021814 A1 1/2007 Inman et al.
2007/0025608 A1 2/2007 Armstrong
2007/0027482 A1 2/2007 Paris et al.
2007/0027483 A1 2/2007 Maschino et al.
2007/0027484 A1 2/2007 Guzman et al.
2007/0027486 A1 2/2007 Armstrong
2007/0027492 A1 2/2007 Maschino et al.
2007/0027496 A1 2/2007 Paris et al.
2007/0027497 A1 2/2007 Paris
2007/0027498 A1 2/2007 Maschino et al.
2007/0027499 A1 2/2007 Maschino et al.
2007/0027500 A1 2/2007 Maschino et al.
2007/0027504 A1 2/2007 Barrett et al.
2007/0055324 A1 3/2007 Thompson et al.
2007/0067004 A1 3/2007 Boveja et al.
2007/0083242 A1 4/2007 Mazgalev et al.
2007/0093434 A1 4/2007 Rossetti et al.
2007/0093870 A1 4/2007 Maschino
2007/0093875 A1 4/2007 Chavan et al.
2007/0100263 A1 5/2007 Merfeld
2007/0100377 A1 5/2007 Armstrong et al.
2007/0100378 A1 5/2007 Maschino
2007/0100380 A1 5/2007 Fukui
2007/0100392 A1 5/2007 Maschino et al.
2007/0106339 A1 5/2007 Errico et al.
2007/0112404 A1 5/2007 Mann et al.
2007/0118177 A1 5/2007 Libbus et al.
2007/0118178 A1 5/2007 Fukui
2007/0129767 A1 6/2007 Wahlstrand
2007/0129780 A1 6/2007 Whitehurst et al.
2007/0135846 A1 6/2007 Knudson et al.
2007/0135856 A1 6/2007 Knudson et al.
2007/0135857 A1 6/2007 Knudson et al.
2007/0135858 A1 6/2007 Knudson et al.
2007/0136098 A1 6/2007 Smythe et al.
2007/0142870 A1 6/2007 Knudson et al.
2007/0142871 A1 6/2007 Libbus et al.
2007/0142874 A1 6/2007 John
2007/0150006 A1 6/2007 Libbus et al.
2007/0150011 A1 6/2007 Meyer et al.
2007/0150021 A1 6/2007 Chen et al.
2007/0150027 A1 6/2007 Rogers
2007/0156180 A1 7/2007 Jaax et al.
2007/0198063 A1 8/2007 Hunter et al.
2007/0239243 A1 10/2007 Moffitt et al.
2007/0244522 A1 10/2007 Overstreet
2007/0250145 A1 10/2007 Kraus et al.
2007/0255320 A1 11/2007 Inman et al.
2007/0255333 A1 11/2007 Giftakis
2007/0255339 A1 11/2007 Torgerson
2008/0021517 A1 1/2008 Dietrich
2008/0021520 A1 1/2008 Dietrich
2008/0045882 A1 2/2008 Finsterwald
2008/0046055 A1 2/2008 Durand et al.
2008/0051852 A1 2/2008 Dietrich et al.
2008/0058871 A1 3/2008 Libbus et al.
2008/0103407 A1 5/2008 Bolea et al.
2008/0140138 A1 6/2008 Ivanova et al.
2008/0183226 A1 7/2008 Buras et al.
2008/0183246 A1 7/2008 Patel et al.
2008/0195171 A1 8/2008 Sharma
2008/0208266 A1 8/2008 Lesser et al.
2008/0213331 A1 9/2008 Gelfand et al.
2008/0234790 A1 9/2008 Bayer et al.
2008/0281197 A1* 11/2008 Wiley .................... C08L 71/02
600/437
2008/0281365 A1 11/2008 Tweden et al.
2008/0281372 A1 11/2008 Libbus et al.
2009/0012590 A1 1/2009 Inman et al.
2009/0048194 A1 2/2009 Aerssens et al.
2009/0082832 A1 3/2009 Carbunaru et al.
2009/0088821 A1 4/2009 Abrahamson
2009/0105782 A1 4/2009 Mickle et al.
2009/0112291 A1 4/2009 Wahlstrand et al.
2009/0123521 A1 5/2009 Weber et al.
2009/0125076 A1 5/2009 Shuros et al.
2009/0125079 A1 5/2009 Armstrong et al.
2009/0171405 A1 7/2009 Craig
2009/0177112 A1 7/2009 Gharib et al.
2009/0187231 A1 7/2009 Errico et al.
2009/0210042 A1 8/2009 Kowalczewski
2009/0248097 A1 10/2009 Tracey et al.
2009/0254143 A1 10/2009 Tweden et al.
2009/0275997 A1 11/2009 Faltys et al.
2009/0276019 A1 11/2009 Perez et al.
2009/0281593 A9 11/2009 Errico et al.
2009/0312817 A1 12/2009 Hogle et al.
2010/0003656 A1 1/2010 Kilgard et al.
2010/0010556 A1 1/2010 Zhao et al.
2010/0010571 A1 1/2010 Skelton et al.
2010/0010581 A1 1/2010 Goetz et al.
2010/0010603 A1 1/2010 Ben-David et al.
2010/0016746 A1 1/2010 Hampton et al.
2010/0042186 A1 2/2010 Ben-David et al.
2010/0063563 A1 3/2010 Craig
2010/0074934 A1 3/2010 Hunter
2010/0191304 A1 7/2010 Scott
2010/0215632 A1 8/2010 Boss et al.
2010/0241183 A1 9/2010 DiLorenzo
2010/0241207 A1 9/2010 Bluger
2010/0249859 A1 9/2010 DiLorenzo
2010/0280562 A1 11/2010 Pi et al.
2010/0280569 A1 11/2010 Bobillier et al.
2011/0004266 A1 1/2011 Sharma
2011/0054569 A1 3/2011 Zitnik et al.
2011/0066208 A1 3/2011 Pasricha et al.
2011/0082515 A1 4/2011 Libbus et al.
2011/0092882 A1 4/2011 Firlik et al.
2011/0144717 A1 6/2011 Burton et al.
2011/0145588 A1 6/2011 Stubbs et al.
2011/0152967 A1 6/2011 Simon et al.

(56) References Cited

U.S. PATENT DOCUMENTS

2011/0178441 A1* 7/2011 Tyler .................... A61N 5/0622 601/2
2011/0224749 A1 9/2011 Ben-David et al.
2011/0247620 A1 10/2011 Armstrong et al.
2011/0275927 A1 11/2011 Wagner et al.
2011/0301658 A1 12/2011 Yoo et al.
2011/0307027 A1 12/2011 Sharma et al.
2012/0053657 A1 3/2012 Parker et al.
2012/0065706 A1 3/2012 Vallapureddy et al.
2012/0071795 A1* 3/2012 Khokhlova .............. A61N 7/02 601/2
2012/0179219 A1 7/2012 Kisker et al.
2012/0185009 A1 7/2012 Komet et al.
2012/0185020 A1 7/2012 Simon et al.
2012/0296176 A1 11/2012 Herbst
2013/0013016 A1 1/2013 Diebold
2013/0018439 A1 1/2013 Chow et al.
2013/0066392 A1 3/2013 Simon et al.
2013/0066395 A1 3/2013 Simon et al.
2013/0150756 A1* 6/2013 Vitek ................... A61B 8/5207 601/2
2013/0245718 A1 9/2013 Birkholz et al.
2013/0317580 A1 11/2013 Simon et al.
2014/0046407 A1 2/2014 Ben-Ezra et al.
2014/0107542 A1 4/2014 Schubert et al.
2014/0148832 A1* 5/2014 Walton ................. A61B 10/025 606/169
2014/0206945 A1 7/2014 Liao
2014/0257425 A1 9/2014 Arcot-Krishnamurthy et al.
2014/0277260 A1 9/2014 Khalil et al.
2014/0288551 A1 9/2014 Bharmi et al.
2014/0330335 A1 11/2014 Errico et al.
2015/0018728 A1 1/2015 Gross et al.
2015/0119956 A1 4/2015 Libbus et al.
2015/0133717 A1 5/2015 Ghiron et al.
2015/0180271 A1 6/2015 Angara et al.
2015/0233904 A1 8/2015 Nayak
2015/0241447 A1 8/2015 Zitnik et al.
2015/0359511 A1 12/2015 Uchiumi et al.
2016/0250097 A9 9/2016 Tracey et al.
2016/0331952 A1 11/2016 Faltys et al.
2016/0367808 A9 12/2016 Simon et al.
2017/0202467 A1 7/2017 Zitnik et al.
2017/0245379 A1 8/2017 Kang
2017/0304621 A1 10/2017 Malbert et al.
2017/0361093 A1 12/2017 Yoo et al.
2017/0368329 A1 12/2017 Tyler et al.
2018/0021217 A1* 1/2018 Tracey ................... A61H 23/00 601/84
2018/0021580 A1 1/2018 Tracey et al.
2018/0085578 A1 3/2018 Rennaker, II et al.
2018/0117320 A1 5/2018 Levine et al.
2018/0207450 A1 7/2018 Sanchez et al.
2018/0289970 A1 10/2018 Faltys et al.
2019/0010535 A1 1/2019 Pujol Onofre et al.
2019/0022389 A1 1/2019 Leonhardt
2019/0030334 A1 1/2019 Lerman et al.
2019/0192847 A1 6/2019 Faltys et al.
2019/0290902 A1 9/2019 Romero-Ortega et al.
2019/0321623 A1 10/2019 Huston et al.
2020/0046992 A1* 2/2020 Tracey ................. A61B 5/6823
2020/0330760 A1 10/2020 Levine et al.
2020/0402656 A1 12/2020 DeBates et al.
2020/0406065 A1* 12/2020 Puleo ................. A61N 1/36034
2021/0251848 A1 8/2021 Tracey et al.
2021/0315505 A1 10/2021 Levine et al.
2021/0353949 A1 11/2021 Faltys et al.
2022/0040483 A1 2/2022 Levine et al.
2022/0072309 A9 3/2022 Levine et al.
2022/0118257 A1 4/2022 Huston et al.
2022/0193413 A1 6/2022 Levine et al.
2022/0212001 A1 7/2022 Faltys et al.
2022/0212012 A1 7/2022 Manogue
2022/0257941 A1 8/2022 Levine et al.
2022/0362555 A1 11/2022 Zitnik et al.
2023/0270996 A1 8/2023 Huston et al.

FOREIGN PATENT DOCUMENTS

| | | | |
|---|---|---|---|
| CN | 101578067 | A | 11/2009 |
| CN | 101868280 | A | 10/2010 |
| CN | 104220129 | A | 12/2014 |
| DE | 2628045 | A1 | 1/1977 |
| DE | 3736664 | A1 | 5/1989 |
| DE | 20316509 | U1 | 4/2004 |
| EP | 0438510 | B1 | 8/1996 |
| EP | 0726791 | B1 | 6/2000 |
| EP | 1001827 | B1 | 1/2004 |
| EP | 2213330 | A2 | 8/2010 |
| EP | 2073896 | B1 | 10/2011 |
| EP | 3470111 | A1 | 4/2019 |
| GB | 04133 | | 2/1910 |
| GB | 2073428 | A | 10/1981 |
| KR | 20050039445 | A | 4/2005 |
| WO | WO93/01862 | A1 | 2/1993 |
| WO | WO97/30998 | A1 | 8/1997 |
| WO | WO98/20868 | A1 | 5/1998 |
| WO | WO00/27381 | A2 | 5/2000 |
| WO | WO00/47104 | A2 | 8/2000 |
| WO | WO01/00273 | A1 | 1/2001 |
| WO | WO01/08617 | A1 | 2/2001 |
| WO | WO01/89526 | A1 | 11/2001 |
| WO | WO02/44176 | A1 | 6/2002 |
| WO | WO02/057275 | A1 | 7/2002 |
| WO | WO03/072135 | A2 | 9/2003 |
| WO | WO2004/000413 | A2 | 12/2003 |
| WO | WO2004/064918 | A1 | 8/2004 |
| WO | WO2005/092308 | A2 | 10/2005 |
| WO | WO2006/073484 | A1 | 7/2006 |
| WO | WO2006/076681 | A2 | 7/2006 |
| WO | WO2007/133718 | A2 | 11/2007 |
| WO | WO2008/112915 | A1 | 9/2008 |
| WO | WO2010/005482 | A1 | 1/2010 |
| WO | WO2010/067360 | A2 | 6/2010 |
| WO | WO2010/118035 | A2 | 10/2010 |
| WO | WO2016/134197 | A1 | 8/2016 |
| WO | WO2018/081826 | A1 | 5/2018 |
| WO | WO2020/006048 | A1 | 1/2020 |
| WO | WO2021/146247 | A1 | 7/2021 |

OTHER PUBLICATIONS

US 11,439,824 B2, 09/2022, Zitnik et al. (withdrawn)

Abraham, Coagulation abnormalities in acute lung injury and sepsis, Am. J. Respir. Cell Mol. Biol., vol. 22(4), pp. 401-404, Apr. 2000.

Aekerlund et al., Anti-inflammatory effects of a new tumour necrosis factor-alpha (TNF-Alpha) inhibitor (CNI-1493) in collagen-induced arthritis (CIA) in rats, Clinical & Experimental Immunology, vol. 115, No. 1, pp. 32-41, Jan. 1, 1999.

Anderson et al.; Reflex principles of immunological homeostasis; Annu. Rev. Immunol.; 30; pp. 313-335; Apr. 2012.

Antonica, A., et al., Vagal control of lymphocyte release from rat thymus, J. Auton. Nerv. Syst., vol. 48(3), pp. 187-197, Aug. 1994.

Asakura et al., Non-surgical therapy for ulcerative colitis, Nippon Geka Gakkai Zasshi, vol. 98, No. 4, pp. 431-437, Apr. 1997 (abstract only).

Beliavskaia et al., "On the effects of prolonged stimulation of the peripheral segment of the vagus nerve . . . ," Fiziologicheskii Zhurnal SSSR Imeni I.M. Sechenova., vol. 52(11); p. 1315-1321, Nov. 1966.

Ben-Noun et al.; Neck circumference as a simple screening measure for identifying overweight and obese patients; Obesity Research; vol. 9; No. 8; pp. 470-477; Aug. 8, 2001.

Benoist, et al., "Mast cells in autoimmune disease" Nature., vol. 420(19): pp. 875-878, Dec. 2002.

Benthem et al.; Parasympathetic inhibition of sympathetic neural activity to the pancreas; Am.J.Physiol Endocrinol.Metab; 280(2); pp. E378-E381; Feb. 2001.

(56) References Cited

OTHER PUBLICATIONS

Bernik et al., Vagus nerve stimulation attenuates cardiac TNF production in endotoxic shock, (supplemental to SHOCK, vol. 15, 2001, Injury, inflammation and sepsis: laboratory and clinical approaches, SHOCK, Abstracts, 24th Annual Conference on Shock, Marco Island, FL, Jun. 9-12, 2001), Abstract No. 81.
Bernik et al., Vagus nerve stimulation attenuates endotoxic shock and cardiac TNF production, 87th Clinical Congress of the American College of Surgeons, New Orleans, LA, Oct. 9, 2001.
Bernik et al., Vagus nerve stimulation attenuates LPS-induced cardiac TNF production and myocardial depression IN shock, New York Surgical Society, New York, NY, Apr. 11, 2001.
Bernik, et al., Pharmacological stimulation of the cholinergic antiinflammatory pathway, The Journal of Experimental Medicine, vol. 195, No. 6, pp. 781-788, Mar. 18, 2002.
Besedovsky, H., et al., Immunoregulatory feedback between interleukin-1 and glucocorticoid hormones, Science, vol. 233, No. 4764, pp. 652-654, Aug. 1986.
Bhattacharya, S.K et al., Central muscarinic receptor subtypes and carrageenin-induced paw oedema in rats, Res. Esp. Med. vol. 191(1), pp. 65-76, Dec. 1991.
Bianchi et al., Suppression of proinflammatory cytokines in monocytes by a tetravalent guanylhydrazone, Journal of Experimental Medicine, vol. 183, pp. 927-936, Mar. 1996.
Biggio et al.; Chronic vagus nerve stimulation induces neuronal plasticity in the rat hippocampus; Int. J. Neurpsychopharmacol.; vol. 12; No. 9; pp. 1209-1221; Oct. 2009.
Blackwell, T. S. et al., Sepsis and cytokines: current status, Br. J. Anaesth., vol. 77(1), pp. 110-117, Jul. 1996.
Blum, A. et al., Role of cytokines in heart failure, Am. Heart J., vol. 135(2), pp. 181-186, Feb. 1998.
Boldyreff, Gastric and intestinal mucus, its properties and physiological importance, Acta Medica Scandinavica (journal), vol. 89, Issue 1-2, pp. 1-14, Jan./Dec. 1936.
Borovikova et al., Acetylcholine inhibition of immune response to bacterial endotoxin in human macrophages, Abstracts, Society for Neuroscience, 29th Annual Meeting, Miami Beach, FL, (Abs. No. 624.6); Oct. 23-28, 1999.
Borovikova et al., Efferent vagus nerve activity attenuates cytokine-mediated inflammation, Society for Neuroscience Abstracts, vol. 26, No. 102, Nov. 4-9, 2000 (abstract only).
Borovikova et al., Intracerebroventricular CNI-1493 prevents LPS-induced hypotension and peak serum TNF at a four-log lower dose than systemic treatment, 21st Annual Conference on Shock, San Antonio, TX, Jun. 14-17, 1998, Abstract No. 86.
Borovikova et al., Role of the efferent vagus nerve signaling in the regulation of the innate immune response to LPS, (supplemental to SHOCK, vol. 13, 2000, Molecular, cellular, and systemic pathobiological aspects and therapeutic approaches, abstracts, 5th World Congress on Trauma, Shock inflammation and sepsis-pathophysiology, immune consequences and therapy, Feb. 29, 2000-Mar. 4, 2000, Munich, DE), Abstract No. 166.
Borovikova et al., Role of the vagus nerve in the anti-inflammatory effects of CNI-1493, the FASEB journal, vol. 14, No. 4, 2000 (Experimental Biology 2000, San Diego, CA, Apr. 15-18, 2000, Abstract No. 97.9).
Borovikova et al., Vagotomy blocks the protective effects of I.C.V. CNI-1493 against LPS-induced shock, (Supplemental to SHOCK, vol. 11, 1999, Molecular, cellular, and systemic pathobioloigal aspects and therapeutic approaches, abstacts and program, Fourth international Shock Congress and 22nd Annual Conference on Shock, Philadelphia, PA, Jun. 12-16, 1999), Abstract No. 277.
Borovikova, L. V., et al., Role of vagus nerve signaling in CNI-1493-mediated suppression of acute inflammation, Autonomic Neuroscience, vol. 85, No. 1-3, pp. 141-147, Dec. 20, 2000.
Borovikova, L. V., et al., Vagus nerve stimulation attenuates the systemic inflammatory response to endotoxin, Nature, vol. 405, No. 6785: pp. 458-462, May 25, 2000.
Bruchfeld et al.; Whole blood cytokine attenuation by cholinergic agonists ex vivo and relationship to vagus nerve activity in rheumatoid arthritis; J. Int. Med.; 268(1); pp. 94-101; Jul. 2010.
Bulloch et al.; Characterization of choline O-acetyltransferase (ChAT) in the BALB/C mouse spleen; Int.J.Neurosci.; 76(1-2); pp. 141-149; May 1994.
Bumgardner, G. L. et al., Transplantation and cytokines, Seminars in Liver Disease, vol. 19, No. 2, Thieme Medical Publishers; pp. 189-204, © 1999.
Bushby et al; Centiles for adult head circumference; Archives of Disease in Childhood; vol. 67(10); pp. 1286-1287; Oct. 1992.
Cano et al.; Characterization of the central nervous system innervation of the rat spleen using viral transneuronal tracing; J.Comp Neurol.; 439(1); pp. 1-18; Oct. 2001.
Caravaca et al.; A novel flexible cuff-like microelectrode for dual purpose, acute and chronic electrical interfacing with the mouse cervical vagus nerve; Journal of Neural Engineering; 14(6);066005; Nov. 1, 2017.
Carteron, N. L., Cytokines in rheumatoid arthritis: trials and tribulations, Mol. Med. Today, vol. 6(8), pp. 315-323, Aug. 2000.
Cavaillon et al.; The pro-inflammatory cytokine casade; Immune Response in the Critically Ill; Springer-Verlag Berlin Hiedelberg; pp. 37-66; Jan. 21, 2002.
Cheyuo et al.; The parasympathetic nervous system in the quest for stroke therapeutics; J. Cereb. Blood Flow Metab.; 31(5); pp. 1187-1195; May 2011.
Cicala et al., "Linkage between inflammation and coagulation: An update on the molecular basis of the crosstalk," Life Sciences, vol. 62(20); pp. 1817-1824. Apr. 1998.
Clark et al.; Enhanced recognition memory following vagus nerve stimulation in human subjects; Nat. Neurosci.; 2(1); pp. 94-98; Jan. 1999.
Cohen, "The immunopathogenesis of sepsis," Nature., vol. 420(6917): pp. 885-891, Dec. 2002.
Corcoran, et al., The effects of vagus nerve stimulation on pro- and anti-inflammatory cytokines in humans: a preliminary report, NeuroimmunoModulation, vol. 12(5), pp. 307-309, Sep. 2005.
Crusz et al.; Inflammation and cancer; advances and new agents; Nature reviews Clinical Oncology; 12(10); pp. 584-596; doi: 10.1038/nrclinonc.2015.105; Jun. 30, 2015.
Dake; Chronic cerebrospinal venous insufficiency and multiple sclerosis: Hostory and background; Techniques Vasc. Intervent. Radiol.; 15(2); pp. 94-100; Jun. 2012.
Das, Critical advances in spticemia and septic shock, Critical Care, vol. 4, pp. 290-296, 7 Sep. 2000.
Del Signore et al; Nicotinic acetylcholine receptor subtypes in the rat sympathetic ganglion: pharmacological characterization, subcellular distribution and effect of pre- and postganglionic nerve crush; J.Neuropathol.Exp. Neurol.; 63(2); pp. 138-150; Feb. 2004.
Diamond et al.; Mapping the immunological homunculus; Proc. Natl. Acad. Sci. USA; 108(9); pp. 3461-3462; Mar. 1, 2011.
Dibbs, Z., et al., Cytokines in heart failure: pathogenetic mechanisms and potential treatment, Proc. Assoc. Am. Physicians, vol. 111, No. 5, pp. 423-428, Sep.-Oct. 1999.
Dinarello, C. A., The interleukin-1 family: 10 years of discovery, FASEB J., vol. 8, No. 15, pp. 1314-1325, Dec. 1994.
Dorr et al.; Effect of vagus nerve stimulation on serotonergic and noradrenergic transmission; J. Pharmacol. Exp. Ther.; 318(2); pp. 890-898; Aug. 2006.
Doshi et al., Evolving role of tissue factor and its pathway inhibitor, Crit. Care Med., vol. 30, suppl. 5, pp. S241-S250, May 2002.
Elenkov et al.; Stress, corticotropin-releasing hormone, glucocorticoids, and the immune / inflammatory response: acute and chronic effects; Ann. N.Y. Acad. Sci.; 876; pp. 1-13; Jun. 22, 1999.
Ellrich et al.; Transcutaneous vagus nerve stimulation; Eur. Neurological Rev.; 6(4); pp. 254-256; Winter 2011.
Engineer et al.; Directing neural plasticity to understand and treat tinnitus; Hear. Res.; 295; pp. 58-66; Jan. 2013.
Engineer et al.; Reversing pathological neural activity using targeted plasticity; Nature; 470(7332); pp. 101-104; Feb. 3, 2011 (Author Manuscript).
Esmon, The protein C pathway, Crit. Care Med., vol. 28, suppl. 9, pp. S44-S48, Sep. 2000.

(56) References Cited

OTHER PUBLICATIONS

Fields; New culprits in chronic pain; Scientific American; pp. 50-57; Nov. 2009.
Fleshner, M., et al., Thermogenic and corticosterone responses to intravenous cytokines (IL-1? and TNF -?) are attenuated by subdiaphragmatic vagotomy, J. Neuroimmunol., vol. 86(2), pp. 134-141, Jun. 1998.
Fox, D. A., Cytokine blockade as a new strategy to treat rheumatoid arthritis, Arch. Intern. Med., vol. 160, pp. 437-444, Feb. 28, 2000.
Fox, et al., Use of muscarinic agonists in the treatment of Sjorgren' syndrome, Clin. Immunol., vol. 101, No. 3; pp. 249-263, Dec. 2001.
Fujii et al.; Simvastatin regulates non-neuronal cholinergic activity in T lymphocytes via CD11a-mediated pathways; J. Neuroimmunol.; 179(1-2); pp. 101-107; Oct. 2006.
Gao et al.; Investigation of specificity of auricular acupuncture points in regulation of autonomic function in anesthetized rats; Autonomic Neurosc.; 138(1-2); pp. 50-56; Feb. 29, 2008.
Gattorno, M., et al., Tumor necrosis factor induced adhesion molecule serum concentrations in henoch-schoenlein purpura and pediatric systemic lupus erythematosus, J. Rheumatol., vol. 27, No. 9, pp. 2251-2255, Sep. 2000.
Gaykema, R. P., et al., Subdiaphragmatic vagotomy suppresses endotoxin-induced activation of hypothalamic corticotropin-releasing hormone neurons and ACTH secretion, Endocrinology, vol. 136, No. 10, pp. 4717-4720, Oct. 1995.
Ghelardini et al., S-(−)-ET 126: A potent and selective M1 antagonist in vitro and in vivo, Life Sciences, vol. 58, No. 12, pp. 991-1000, Feb. 1996.
Ghia, et al., The vagus nerve: a tonic inhibitory influence associated with inflammatory bowel disease in a murine model, Gastroenterology, vol. 131, No. 4, pp. 1122-1130, Oct. 2006.
Giebelen, et al., Stimulation of ?7 cholinergic receptors inhibits lipopolysaccharide-induced neutrophil recruitment by a tumor necrosis factor ?-independent mechanism, SHOCK, vol. 27, No. 4, pp. 443-447, Apr. 2007.
Goyal et al., Nature of the vagal inhibitory innervation to the lower esophageal sphincter, Journal of Clinical Investigation, vol. 55, pp. 1119-1126, May 1975.
Gracie, J. A., et al., A proinflammatory role for IL-18 in rheumatoid arthritis, J. Clin. Invest., vol. 104, No. 10, pp. 1393-1401, Nov. 1999.
Granert et al., Suppression of macrophage activation with CNI-1493 increases survival in infant rats with systemic haemophilus influenzae infection, Infection and Immunity, vol. 68, No. 9, pp. 5329-5334, Sep. 2000.
Green et al., Feedback technique for deep relaxation, Psycophysiology, vol. 6, No. 3, pp. 371-377, Nov. 1969.
Gregory et al., Neutrophil-kupffer-cell interaction in host defenses to systemic infections, Immunology Today, vol. 19, No. 11, pp. 507-510, Nov. 1998.
Groves et al.; Recordings from the rat locus coeruleus during acute vagal nerve stimulation in the anaesthetised rat; Neuroscience Letters; 379(3); pp. 174-179; May 13, 2005.
Guarente, Leonard, Ph. D.; Sirtuins, Aging, and Medicine; N Engl J Med ; vol. 364:pp. 2235-2244; Jun. 2011.
Guslandi, M., Nicotine treatment for ulcerative colitis, Br. J. Clin. Pharmacol., vol. 48(4), pp. 481-484, Oct. 1999.
Hansson, E.; Could chronic pain and spread of pain sensation be induced and maintained by glial activation ?. Acta Physiologica, vol. 187, Issue 1-2; pp. 321R327, May/Jun. 2006.
Harrison's Principles of Internal Medicine, 13th Ed., pp. 511-515 and 1433-1435, Mar. 1994.
Hatton et al.; Vagal nerve stimulation: overview and implications for anesthesiologists; Int'l Anesthesia Research Society; vol. 103; No. 5; pp. 1241-1249; Nov. 2006.
Hirano, T., Cytokine suppresive agent improves survival rate in rats with acute pancreatitis of closed duodenal loop, J. Surg. Res., vol. 81, No. 2, pp. 224-229, Feb. 1999.
Hoffer et al.; Implantable electrical and mechanical interfaces with nerve and muscle; Annals of Biomedical Engineering; vol. 8; pp. 351-360; Jul. 1980.
Hommes, D. W. et al., Anti- and Pro-inflammatory cytokines in the pathogenesis of tissue damage in Crohn's disease, Current Opinion in Clinical Nutrition and Metabolic Care, vol. 3(3), pp. 191-195, May 2000.
Housley et al.; Biomarkers in multiple sclerosis; Clinical Immunology; 161 (1); pp. 51-58; Nov. 2015.
Hsu, et al., Analysis of efficiency of magnetic stimulation, IEEE Trans. Biomed. Eng., vol. 50(11), pp. 1276-1285, Nov. 2003.
Hsu, H. Y., et al., Cytokine release of peripheral blood monoculear cells in children with chronic hepatitis B virus infection, J. Pediatr. Gastroenterol., vol. 29, No. 5, pp. 540-545, Nov. 1999.
Hu, et al., The effect of norepinephrine on endotoxin-mediated macrophage activation, J. Neuroimmunol., vol. 31(1), pp. 35-42, Jan. 1991.
Huston et al.; Splenectomy inactivates the cholinergic antiinflammatory pathway during lethal endotoxemia and polymicrobial sepsis; J. Exp. Med. 2006; vol. 203, No. 7; pp. 1623-1628; Jun. 19, 2006.
Huston et al.; Transcutaneous vagus nerve stimulation reduces serum high mobility group box 1 levels and improves survival in murine sepsis; Crit. Care Med.; 35(12); pp. 2762-2768; Dec. 2007.
Hutchinson et al.; Proinflammatory cytokines oppose opioid induced acute and chronic analgesia; Brain Behav Immun.; vol. 22; No. 8; pp. 1178-1189; Nov. 2008.
Ilton et al., "Differential expression of neutrophil adhesion molecules during coronary artery surgery with cardiopulmonary bypass" Journal of Thoracic and Cardiovascular Surgery, Mosby- Year Book, inc., St. Louis, MO, US, pp. 930-937, Nov. 1, 1999.
Jander, S. et al., Interleukin-18 is induced in acute inflammatory demyelinating polymeuropathy, J. Neuroimmunol., vol. 114, pp. 253-258, Mar. 2001.
Kalishevskaya et al. "The character of vagotomy-and atropin-induced hypercoagulation," Sechenov Physiological Journal of the USSR, 65(3): pp. 398-404, Mar. 1979.
Kalishevskaya et al.; Nervous regulation of the fluid state of the blood; Usp. Fiziol. Nauk;, vol. 13; No. 2; pp. 93-122; Apr.-Jun. 1982.
Kanai, T. et al., Interleukin-18 and Crohn's disease, Digestion, vol. 63, suppl. 1, pp. 37-42; 2001 (year of pub. sufficiently earlier than effective US filing date and any foreign priority date).
Katagiri, M., et al., Increased cytokine production by gastric mucosa in patients with helicobacter pylori infection, J. Clin, Gastroenterol., vol. 25, Suppl. 1, pp. S211-S214, 1997.
Katsavos et al.; Biomarkers in multiple sclerosis: an up-to-date overview; Multiple Sclerosis International; vol. 2013, Article ID 340508, 20 pages; 2013 (the year of publication is sufficiently earlier than the effective U.S. filing date and any foreign priority date so that the particular month of publication is not in issue).
Kawahara et al.; SIRT6 links histone H3 lysine 9 deacetylation to NF-kappaB-dependent gene expression and organismal life span.; Cell. ; vol. 136; No. 1; pp. 62-74; Jan. 2009.
Kawashima, et al., Extraneuronal cholinergic system in lymphocytes, Pharmacology & Therapeutics, vol. 86, pp. 29-48, Apr. 2000.
Kees et al; Via beta-adrenoceptors, stimulation of extrasplenic sympathetic nerve fibers inhibits lipopolysaccharide-induced TNF secretion in perfused rat spleen; J.Neuroimmunol.; 145(1-2); pp. 77-85; Dec. 2003.
Khatun, S., et al., "Induction of hypercoagulability condition by chronic localized cold stress in rabbits," Thromb. and Haemost., 81(3): pp. 449-455, Mar. 1999.
Kimball, et al., Levamisole causes differential cytokine expression by elicited mouse peritoneal macrophases, Journal of Leukocyte Biology, vo. 52, No. 3, pp. 349-356, Sep. 1992 (abstract only).
Kimmings, A. N., et al., Systemic inflammatory response in acute cholangitis and after subsequent treatment, Eur. J. Surg., vol. 166, pp. 700-705, Sep. 2000.
Kirchner et al.; Left vagus nerve stimulation suppresses experimentally induced pain; Neurology; vol. 55; pp. 1167-1171; Oct. 2000.

(56) References Cited

OTHER PUBLICATIONS

Kokkula, R. et al., Successful treatment of collagen-induced arthritis in mice and rats by targeting extracellular high mobility group box chromosomal protein 1 activity, Arthritis Rheum., 48(7), pp. 2052-2058, Jul. 2003.
Koopman et al.; Pilot study of stimulation of the cholinergic anti-inflammatory pathway with an implantable vagus nerve stimulation device in patients with rheumatoid arthritis; Arth. Rheum.; 64(10 suppl.); pp. S195; Oct. 2012.
Koopman et al., Pilot study of stimulation of the cholinergic anti-inflammatory pathway with an implantable vagus nerve stimulation device in patients with rheumatoid arthritis; 2012 ACR/ARHP Annual Meeting; Abstract No. 451; 4 pages; retrieved from the internet (https://acrabstracts.org/abstract/pilot-study-of-stimulation-of-the-cholinergic-anti-inflammatory-pathway-with-an-implantable-vagus-nerve-sti mulation-device-in-patients-with-rheumatoid-arthritis); (Abstract Only); on Sep. 24, 2020.
Koopman et al.; THU0237 first-in-human study of vagus nerve stimulation for rheumatoid arthritis: clinical and biomarker results through day 84; Annals of the Rheumatic Diseases; 72(Suppl 3):A246; Jun. 1, 2013 (Abstract Only).
Koopman et al.; Vagus nerve stimulation inhibits cytokine production and attenuates disease severity in rheumatoid arthritis; Proceedings of the National Academy of Sciences; 113(29); pp. 8284-8289; Jul. 19, 2016.
Krarup et al; Conduction studies in peripheral cat nerve using implanted electrodes: I. methods and findings in controls; Muscle & Nerve; vol. 11; pp. 922-932; Sep. 1988.
Kudrjashov, et al. "Reflex nature of the physiological anticoagulating system," Nature, vol. 196(4855): pp. 647-649; Nov. 17, 1962.
Kumins, N. H., et al., Partial hepatectomy reduces the endotoxin-induced peak circulating level of tumor necrosis factor in rats, SHOCK, vol. 5, No. 5, pp. 385-388, May 1996.
Kuznik, "Role of the vascular wall in the process of hemostatis," Usp Sovrem Biol., vol. 75(1): pp. 61-85; 1973 (the year of publication is sufficiently earlier than the effective U.S. filing date and any foreign priority date so that the particular month of publication is not in issue).
Kuznik, et al., "Blood Coagulation in stimulation of the vagus nerve in cats," Biull. Eskp. Biol. Med., vol. 78 (7): pp. 7-9; 1974 (the year of publication is sufficiently earlier than the effective U.S. filing date and any foreign priority date so that the particular month of publication is not in issue).
Kuznik, et al., "Heart as an efferent regulator of the process of blood coagulation and fibrinolysis," Kardiologiia, vol. 13 (3): pp. 10-17; 1973 (the year of publication is sufficiently earlier than the effective U.S. filing date and any foreign priority date so that the particular month of publication is not in issue).
Kuznik, et al., "Role of the heart and vessels in regulating blood coagulation and fibrinolysis," Kagdiologiia, vol. 13(4): pp. 145-154, Apr. 1973.
Kuznik, et al., "Secretion of blood coagulation factors into saliva under conditions of hypo-and hypercoagulation," Voprosy Meditsinskoi Khimil, vol. 19(1): pp. 54-57; 1973(the year of publication is sufficiently earlier than the effective U.S. filing date and any foreign priority date so that the particular month of publication is not in issue).
Kuznik, et al., "The dynamics of procoagulatible and fibrinolytic activities during electrical stimulation of peripheral nerves," Sechenov Physiological Journal of the USSR, vol. 65; No. 3: pp. 414-420, Mar. 1979.
Kuznik, et al., "The role of the vascular wall in the mechanism of control of blood coagulation and fibrinolysis on stimulation of the vagus nerve," Cor Vasa, vol. 17(2): pp. 151-158; 1975 (the year of publication is sufficiently earlier than the effective U.S. filing date and any foreign priority date so that the particular month of publication is not in issue).
Lang, et al., "Neurogienic control of cerebral blood flow," Experimental Neurology, 43(1): pp. 143-161, Apr. 1974.
Lee, H. G., et al., Peritoneal lavage fluids stimulate NIH3T3 fibroblast proliferation and contain increased tumour necrosis factor and IL6 in experimental silica-induced rat peritonitis, Clin. Exp. Immunol., vol. 100, pp. 139-144, Apr. 1995.
Lips et al.; Coexpression and spatial association of nicotinic acetylcholine receptor subunits alpha7 and alpha10 in rat sympathetic neurons; J.Mol.Neurosci.; 30; pp. 15-16; Feb. 2006.
Lipton, J. M. et al.; Anti-inflammatory actions of the neuroimmunomodulator ?-MSH, Immunol. Today, vol. 18, pp. 140-145, Mar. 1997.
Loeb et al.; Cuff electrodes for chronic stimulation and recording of peripheral nerve activity; Journal of Neuroscience Methods; vol. 64; pp. 95-103; Jan. 1996.
Mayo Clinic; The factsheet of vagus nerve stimulation from the Mayo Clinic website: www.mayoclinic.org/tests-procedures/vagus-nerve-sti mulation/about/pac-20384565; retrieved from the internet on Sep. 28, 2021.
Madretsma, G. S., et al., Nicotine inhibits the in vitro production of interleukin 2 and tumour necrosis factor-alpha by human monocuclear cells, Immunopharmacology, vol. 35, No. 1, pp. 47-51, Oct. 1996.
Manta et al.; Optimization of vagus nerve stimulation parameters using the firing activity of serotonin neurons in the rat dorsal raphe; European Neuropsychopharmacology; vol. 19; pp. 250-255; Jan. 2009 (doi: 10.1016/j.euroneuro.2008.12.001).
Martindale: The Extra Pharmacopoeia; 28th Ed. London; The Pharmaceutical Press; pp. 446-485; © 1982.
Martiney et al., Prevention and treatment of experimental autoimmune encephalomyelitis by CNI-1493, a macrophage-deactivating agent, Journal of Immunology, vol. 160, No. 11, pp. 5588-5595, Jun. 1, 1998.
Mcguinness, P. H., et al., Increases in intrahepatic CD68 positive cells, MAC387 positive cells, and proinflammatory cytokines (particulary interleukin 16) in chronic hepatitis C infection, Gut, vol. 46(2), pp. 260-269, Feb. 2000.
Miguel-Hidalgo, J.J.; The role of glial cells in drug abuse; Current Drug Abuse Reviews; vol. 2; No. 1; pp. 76-82; Jan. 2009.
Milligan et al.; Pathological and protective roles of glia in chronic pain; Nat Rev Neurosci.; vol. 10; No. 1; pp. 23-26; Jan. 2009.
Minnich et al.; Anti-cytokine and anti-inflammatory therapies for the treatment of severe sepsis: progress and pitfalls; Proceedings of the Nutrition Society; vol. 63(3); pp. 437-441; Aug. 2004.
Mishchenko, et al., "Coagulation of the blood and fibrinolysos in dogs during vagal stimulation," Sechenov Physiological Journal of the USSR, vol. 61(1): pp. 101-107, 1975.
Mishchenko, "The role of specific adreno-and choline-receptors of the vascular wall in the regulation of blood coagulation in the stimulation of the vagus nerve," Biull. Eskp. Biol. Med., vol. 78(8): pp. 19-22, 1974.
Molina et al., CNI-1493 attenuates hemodynamic and pro-inflammatory responses to LPS, Shock, vol. 10, No. 5, pp. 329-334, Nov. 1998.
Nathan, C. F., Secretory products of macrophages, J. Clin. Invest., vol. 79 (2), pp. 319-326, Feb. 1987.
Navalkar et al.; Irbesartan, an angiotensin type 1 receptor inhibitor, regulates markers of inflammation in patients with premature atherosclerosis; Journal of the American College of Cardiology; vol. 37; No. 2; pp. 440-444; Feb. 2001.
Navzer et al.; Reversing pathological neural activity using targeted plasticity; Nature; 470(7332); pp. 101-104; Feb. 3, 2011.
Neuhaus et al.; P300 is enhanced in responders to vagus nerve stimulation for treatment of major depressive disorder; J. Affect. Disord.; 100(1-3); pp. 123-128; Jun. 2007.
Noguchi et al., Increases in Gastric acidity in response to electroacupuncture stimulation of hindlimb of anesthetized rats, Jpn. J. Physiol., 46(1), pp. 53-58, Feb. 1996.
Norton, Can ultrasound be used to stimulate nerve tissue, BioMedical Engineering OnLine, 2(1), p. 6, Mar. 4, 2003.
Olofsson et al.; Rethinking inflammation: neural circuits in the regulation of immunity; Immunological Reviews; 248(1); pp. 188-204; Jul. 2012.
Oshinsky et al.; Non-invasive vagus nerve stimulation as treatment for trigeminal allodynia; Pain; 155(5); pp. 1037-1042; May 2014.

(56) References Cited

OTHER PUBLICATIONS

Palmblad et al., Dynamics of early synovial cytokine expression in rodent collagen-induced arthritis: a thereapeutic study unding a macrophage-deactivation compound, American Journal of Pathology, vol. 158, No. 2, pp. 491-500, Feb. 2, 2001.
Pateyuk, et al., "Treatment of Botkin's disease with heparin," Klin. Med., vol. 51(3): pp. 113-117, Mar. 1973.
Pavlov et al; Controlling inflammation: the cholinergic anti-inflammatory pathway; Biochem. Soc. Trans.; 34(Pt 6); pp. 1037-1040; Dec. 2006.
Pavlov et al.; The cholinergic anti-inflammatory pathway; Brain, Behavior, and Immunity; 19; p. 493-499; Nov. 2005.
Palov et al.; The cholinergic anti-inflammatory pathway: a missing link in neuroimmunomodulation; Molecular Medicine; 9(5); pp. 125-134; May 2003.
Payne, J. B. et al., Nicotine effects on PGE2 and IL-1 beta release by LPS-treated human monocytes, J. Perio. Res., vol. 31, No. 2, pp. 99-104, Feb. 1996.
Peuker; The nerve supply of the human auricle; Clin. Anat.; 15(1); pp. 35-37; Jan. 2002.
Pongratz et al.; The sympathetic nervous response in inflammation; Arthritis Research and Therapy; 16(504); 12 pages; retrieved from the internet (http://arthritis-research.com/content/16/6/504) ; Jan. 2014.
Prystowsky, J. B. et al., Interleukin-1 mediates guinea pig gallbladder inflammation in vivo, J. Surg. Res., vol. 71, No. 2, pp. 123-126, Aug. 1997.
Pulkki, K. J., Cytokines and cardiomyocyte death, Ann. Med., vol. 29(4), pp. 339-343, Aug. 1997.
Pullan, R. D., et al., Transdermal nicotine for active ulceratiive colitis, N. Engl. J. Med., vol. 330, No. 12, pp. 811-815, Mar. 24, 1994.
Pulvirenti et al; Drug dependence as a disorder of neural plasticity:focus on dopamine and glutamate; Rev Neurosci.; vol. 12; No. 2; pp. 141-158; Apr./Jun. 2001.
Rahman et al.; Mammalian Sirt 1: Insights on its biological functions; Cell Communications and Signaling; vol. 9; No. 11; pp. 1-8; May 2011.
Rayner, S. A. et al., Local bioactive tumour necrosis factor (TNF) in corneal allotransplantation, Clin. Exp. Immunol., vol. 122, pp. 109-116, Oct. 2000.
Reale et al.; Treatment with an acetylcholinesterase inhibitor in alzheimer patients modulates the expression and production of the pro-inflammatory and anti-inflammatory cytokines; J. Neuroimmunology; 148(1-2); pp. 162-171; Mar. 2004.
Rinner et al.; Rat lymphocytes produce and secrete acetylcholine in dependence of differentiation and activation; J.Neuroimmunol.; 81(1-2); pp. 31-37; Jan. 1998.
Robinson et al.; Studies with the Electrocardiogram the Action of the Vagus Nerve on the Human Heart; J Exp Med; 14(3):217-234; Sep. 1911.
Romanovsky, A. A., et al., The vagus nerve in the thermoregulatory response to systemic inflammation, Am. J. Physiol., vol. 273, No. 1 (part 2), pp. R407-R413, Jul. 1, 1997.
Saghizadeh et al.; The expression of TNF? by human muscle; J. Clin. Invest.; vol. 97; No. 4; pp. 1111-1116; Feb. 15, 1996.
Saindon et al.; Effect of cervical vagotomy on sympathetic nerve responses to peripheral interleukin-1beta; Auton.Neuroscience Basic and Clinical; 87; pp. 243-248; Mar. 23, 2001.
Saito, Involvement of muscarinic M1 receptor in the central pathway of the serotonin-induced bezold-jarisch reflex in rats, J. Autonomic Nervous System, vol. 49, pp. 61-68, Sep. 1994.
Sandborn, W. J., et al., Transdermal nicotine for mildly to moderately active ulcerative colitis, Ann. Intern. Med, vol. 126, No. 5, pp. 364-371, Mar. 1, 1997.
Sato, E., et al., Acetylcholine stimulates alveolar macrophages to release inflammatory cell chemotactic activity, Am. J. Physiol., vol. 274, pp. L970-L979, Jun. 1998.
Sato, K.Z., et al., Diversity of mRNA expression for muscarinic acetylcholine receptor subtypes and neuronal nicotinic acetylcholine receptor subunits in human mononuclear leukosytes and leukemic cell lines, Neuroscience Letters, vol. 266, pp. 17-20, Apr. 30, 1999.
Scheinman, R. I., et al., Role of transcriptional activation of I?B? in mediation of immunosuppression by glucocorticoids, Science, vol. 270, No. 5234, pp. 283-286, Oct. 13, 1995.
Shafer, Genotypic testing for human immunodeficiency virus type 1 drug resistance, Clinical Microbiology Reviews, vol. 15, pp. 247-277, Apr. 2002.
Shapiro et al.; Prospective, randomised trial of two doses of rFVIIa (NovoSeven) in haemophilia patients with inhibitors undergoing surgery; Thromb Haemost; vol. 80(5); pp. 773-778; Nov. 1998.
Sher, M. E., et al., The influence of cigarette smoking on cytokine levels in patients with inflammatory bowel disease, Inflamm. Bowel Dis., vol. 5, No. 2, pp. 73-78, May 1999.
Shi et al.; Effects of efferent vagus nerve excitation on inflammatory response in heart tissue in rats with endotoxemia; vol. 15, No. 1; pp. 26-28; Jan. 2003 (Eng. Abstract).
Sokratov, et al. "The role of choline and adrenegic structures in regulation of renal excretion of hemocoagulating compounds into the urine," Sechenov Physiological Journal of the USSR, vol. 63(12): pp. 1728-1732, 1977.
Stalcup et al., Endothelial cell functions in the hemodynamic responses to stress, Annals of the New York Academy of Sciences, vol. 401, pp. 117-131, Dec. 1982.
Steinlein, New functions for nicotine acetylcholine receptors?, Behavioural Brain Res., vol. 95(1), pp. 31-35, Sep. 1998.
Sternberg, E. M., Perspectives series: cytokines and the brain 'neural-immune interactions in health and disease,' J. Clin. Invest., vol. 100, No. 22, pp. 2641-2647, Dec. 1997.
Stevens et al.; The anti-inflammatory effect of some immunosuppressive agents; J. Path.; 97(2); pp. 367-373; Feb. 1969.
Strojnik et al.; Treatment of drop foot using and implantable peroneal underknee stimulator; Scand. J. Rehab. Med.; vol. 19(1); pp. 37R43; Dec. 1986.
Strowig et al.; Inflammasomes in health and disease; Nature; vol. 481; pp. 278-286; doi: 10.1038/nature10759; Jan. 19, 2012.
Sugano et al., Nicotine Inhibits the production of inflammatory mediators in U937 cells through modulation of nuclear factor-kappaβ activation, Biochemical and Biophysical Research Communications, vol. 252, No. 1, pp. 25-28, Nov. 9, 1998.
Suter et al.; Do glial cells control pain ?; Neuron Glia Biol.; vol. 3; No. 3; pp. 255-268; Aug. 2007.
Swick et al.; Locus coeruleus neuronal activity in awake monkeys: relationship to auditory P300-like potentials and spontaneous EEG. Exp. Brain Res.; 101(1); pp. 86-92; Sep. 1994.
Sykes, et al., An investigation into the effect and mechanisms of action of nicotine in inflammatory bowel disease, Inflamm. Res., vol. 49, pp. 311-319, Jul. 2000.
Takeuchi et al., A comparison between chinese blended medicine "Shoseiryuto" tranilast and ketotifen on the anit-allergic action in the guinea pigs, Allergy, vol. 34, No. 6, pp. 387-393, Jun. 1985 (eng. abstract).
Tekdemir et al.; A clinico-anatomic study of the auricular branch of the vagus nerve and arnold's ear-cough reflex; Surg. Radiol. Anat.; 20(4); pp. 253-257; Mar. 1998.
Toyabe, et al., Identification of nicotinic acetylcholine receptors on lymphocytes in the periphery as well as thymus in mice, Immunology, vol. 92(2), pp. 201-205, Oct. 1997.
Tracey et al., Mind over immunity, Faseb Journal, vol. 15, No. 9, pp. 1575-1576, Jul. 2001.
Tracey, K. J. et al., Anti-cachectin/TNF monoclonal antibodies prevent septic shock during lethal bacteraemia; Nature, 330: pp. 662-664, Dec. 23, 1987.
Tracey, K. J. et al., Physiology and immunology of the cholinergic antiinflammatory pathway; J Clin Invest.; vol. 117: No. 2; pp. 289-296; Feb. 2007.
Tracey, K. J. et al., Shock and tissue injury induced by recombinant human cachectin, Science, vol. 234, pp. 470-474, Oct. 24, 1986.
Tracey, K. J.; Reflex control of immunity; Nat Rev Immunol; 9(6); pp. 418-428; Jun. 2009.
Tsutsui, H., et al., Pathophysiologie18 in inflammatory liver diseases; Immunol. Rev., 174:192-209, Apr. 2000.

(56) References Cited

OTHER PUBLICATIONS

Van Der Horst et al.; Stressing the role of FoxO proteins in lifespan and disease; Nat Rev Mol Cell Biol.; vol. 8; No. 6; pp. 440-450; Jun. 2007.
Van Dijk, A. P., et al., Transdermal nictotine inhibits interleukin 2 synthesis by mononuclear cells derived from healthy volunteers, Eur. J. Clin. Invest, vol. 28, pp. 664-671, Aug. 1998.
Vanhoutte, et al., Muscarinic and beta-adrenergic prejunctional modulation of adrenergic neurotransmission in the blood vessel wall, Gen Pharmac., vol. 14(1), pp. 35-37, Jan. 1983.
VanWesterloo, et al., The cholinergic anti-inflammatory pathway regulates the host response during septic peritonitis, The Journal of Infectious Diseases, vol. 191, pp. 2138-2148, Jun. 15, 2005.
Ventureyra, Transcutaneous vagus nerve stimulation for partial onset seizure therapy, Child's Nerv Syst, vol. 16(2), pp. 101-102, Feb. 2000.
Vijayaraghavan, S.; Glial-neuronal interactions-implications for plasticity anddrug addictionl AAPS J.; vol. 11; No. 1; pp. 123-132; Mar. 2009.
Villa et al., Protection against lethal polymicrobial sepsis by CNI-1493, an inhibitor of pro-inflammatory cytokine synthesis, Journal of Endotoxin Research, vol. 4, No. 3, pp. 197-204, Jun. 1997.
Von Känel, et al., Effects of non-specific ?-adrenergic stimulation and blockade on blood coagulation in hypertension, J. Appl. Physiol., vol. 94, pp. 1455-1459, Apr. 2003.
Von Känel, et al., Effects of sympathetic activation by adrenergic infusions on hemostasis in vivo, Eur. J. Haematol., vol. 65: pp. 357-369, Dec. 2000.
Walland et al., Compensation of muscarinic brochial effects of talsaclidine by concomitant sympathetic activation in guinea pigs; European Journal of Pharmacology, vol. 330(2-3), pp. 213-219, Jul. 9, 1997.
Wang et al; Nicotinic acetylcholine receptor alpha7 subunit is an essential regulator of inflammation; Nature; 421; 384-388; Jan. 23, 2003.
Wang, H., et al., HMG-1 as a late mediator of endotoxin lethality in mice, Science, vol. 285, pp. 248-251, Jul. 9, 1999.
Waserman, S. et al., TNF-? dysregulation in asthma: relationship to ongoing corticosteroid therapy, Can. Respir. J., vol. 7, No. 3, pp. 229-237, May-Jun. 2000.
Watanabe, H. et al., The significance of tumor necrosis factor (TNF) levels for rejection of joint allograft, J. Reconstr. Microsurg., vol. 13, No. 3, pp. 193-197, Apr. 1997.
Wathey, J.C. et al., Numerical reconstruction of the quantal event at nicotinic synapses; Biophys. J., vol. 27: pp. 145-164, Jul. 1979.
Watkins, L.R. et al., Blockade of interleukin-1 induced hyperthermia by subdiaphragmatic vagotomy: evidence for vagal mediation of immune-brain communication, Neurosci. Lett., vol. 183(1-2), pp. 27-31, Jan. 1995.
Watkins, L.R. et al., Implications of immune-to-brain communication for sickness and pain, Proc. Natl. Acad. Sci. U.S.A., vol. 96(14), pp. 7710-7713, Jul. 6, 1999.
Webster's Dictionary, definition of "intrathecal", online version accessed Apr. 21, 2009.
Weiner, et al., "Inflammation and therapeutic vaccination in CNS diseases," Nature., vol. 420(6917): pp. 879-884, Dec. 19-26, 2002.
Westerheide et al.; Stress-inducible regulation of heat shock factor 1 by the deacetylase SIRT1.; Science; Vo. 323; No. 5717; pp. 1063-1066; Feb. 2009.
Whaley, K. et al., C2 synthesis by human monocytes is modulated by a nicotinic cholinergic receptor, Nature, vol. 293, pp. 580-582, Oct. 15, 1981.
Woiciechowsky, C. et al., Sympathetic activation triggers systemic interleukin-10 release in immunodepression induced by brain injury, Nature Med., vol. 4, No. 7, pp. 808-813, Jul. 1998.
Yeh, S.S. et al., Geriatric cachexia: the role of cytokines, Am. J. Clin. Nutr., vol. 70(2), pp. 183-197, Aug. 1999.
Yu et al.; Low-level transcutaneous electrical stimulation of the auricular branch of the vagus nerve: a non-invasive approach to treat the initial phase of atrial fibrillation; Heart Rhythm; 10(3); pp. 428-435; Mar. 2013.
Zamotrinsky et al.; Vagal neurostimulation in patients with coronary artery disease; Auton. Neurosci.; 88(1-2); pp. 109-116; Apr. 2001.
Zhang et al., Tumor necrosis factor, The Cytokine Handbook, 3rd ed., Ed. Thompson, Academic Press, pp. 517-548, Jul. 1, 1998.
Zhang et al.; Chronic vagus nerve stimulation improves autonomic control and attenuates systemic inflammation and heart failure progression in a canine high-rate pacing model; Circulation Heart Fail.; 2; pp. 692-699; Nov. 2009.
Zhang et al.; Roles of SIRT1 in the acute and restorative phases following induction of inflammation.; J Biol Chem.; vol. 285; No. 53; pp. 41391-401; Dec. 2010.
Zhao et al.; Transcutaneous auricular vagus stimulation protects endotoxeric rat from lipopolysaccharide-induced inflammation; Evid. Based Complement Alternat. Med.; vol. 2012; Article ID 627023; 10 pages; Dec. 29, 2012.
Zitnik et al.; Treatment of chronic inflammatory diseases with implantable medical devices; Cleveland Clinic Journal of Medicine; 78(Suppl 1); pp. S30-S34; Aug. 2011.
Faltys et al.; U.S. Appl. No. 17/751,505 entitled "Implantable neurostimulator having power control and thermal regulation and methods of use," filed May 23, 2022.
Burke et al., Bent pseudoknots and novel RNA inhibitors of type 1 human immunodeficiency virus (HIV-1) reverse transcriptase, J. Mol. Biol., vol. 264(4); pp. 650-666, Dec. 1996.
Ellington et al., In vitro selection of RNA molecules that bind specific ligands, Nature, vol. 346, pp. 818-822, Aug. 30, 1990.
Holladay et al., Neuronal nicotinic acetylcholine receptors as targets for drug discovery, Journal of Medicinal Chemistry, 40(26), pp. 4169-4194, Dec. 1997.
Hirao et al., The limits of specificity: an experimental analysis with RNA aptamers to MS2 coat protein variants, Mol. Divers., vol. 4, No. 2, pp. 75-89, 1999 (Accepted Jan. 13, 1999).
Jaeger et al., The structure of HIV-1 reverse transcriptase complexed with an RNA pseudoknot inhibitor, The EMBO Journal, 17(15), pp. 4535-4542, Aug. 1998.
Joshi et al., Potent inhibition of human immunodeficiency virus type 1 replection by template analog reverse transcriptase , J. Virol., 76(13), pp. 6545-6557, Jul. 2002.
Kensch et al., HIV-1 reverse transcriptase-pseudoknot RNA aptamer interaction has a binding affinity in the low picomolar range coupled with high specificity, J. Biol. Chem., 275(24), pp. 18271-18278, Jun. 16, 2000.
Lenovere, N. et al., Molecular evolution of the nicotinic acetylcholine receptor: an example of multigene family in excitable cells, J. Mol. Evol., 40, pp. 155-172, Feb. 1995.
Leonard, S. et al., Neuronal nicotinic receptors: from structure to function, Nicotine & Tobacco Res. 3:203-223, Aug. 2001.
Nadol et al., "Surgery of the Ear and Temporal Bone," Lippinkott Williams & Wilkins, 2nd Ed., 2005, (Publication date: Sep. 21, 2004), p. 580.
Nagashima et al., Thrombin-activatable fibrinolysis inhibitor (TAFI) deficiency is compatible with murine life, J. Clin. Invest., 109, pp. 101-110, Jan. 2002.
Schneider et al., High-affinity ssDNA inhibitors of the review transcriptase of type 1 human immunodeficiency virus, Biochemistry, 34(29), pp. 9599-9610, Jul. 1995.
Snyder et al., Correction of hemophilia B in canine and murine models using recombinant adeno-associated viral vectors; Nature Medicine, 5(1), pp. 64-70, Jan. 1999.
Tracey, K.J., The inflammatory reflex, Nature, vol. 420, pp. 853-859, Dec. 19-26, 2002.
Tuerk et al., RNA pseudoknots that inhibit human immunodeficiency virus type 1 reverse transcriptase; Proc. Natl. Acad. Sci. USA, 89, pp. 6988-6992, Aug. 1992.
Tuerk et al., Systematic evolution of ligands by exponential enrichment: RNA ligands to bacteriophage T4 DNA polymerase; Science, 249(4968), pp. 505-510, Aug. 3, 1990.

(56) References Cited

OTHER PUBLICATIONS

Wikipedia; Trigeminal Nerve; retireved from the internet (http://en.wikipedia.org/wiki/Trigeminal_nerve) on Sep. 6, 2022; 12 pages.

* cited by examiner

TREATING BLEEDING AND BLEEDING DISORDERS VIA HIGH INTENSITY FOCUSED ULTRASOUND STIMULATION OF THE SPLEEN

CROSS REFERENCE TO RELATED APPLICATIONS

This patent application is a national phase application under 35 USC 371 of International Patent No. PCT/US2021/013190, titled "TREATING BLEEDING AND BLEEDING DISORDERS VIA HIGH INTENSITY FOCUSED ULTRASOUND STIMULATION OF THE SPLEEN," filed on Jan. 13, 2021, now International Patent Application Publication No. WO 2021/146247, claims priority to U.S. Provisional Patent Application No. 62/960,612, titled "TREATING BLEEDING AND BLEEDING DISORDERS VIA HIGH INTENSITY FOCUSED ULTRASOUND STIMULATION OF THE SPLEEN," and filed on Jan. 13, 2020. Each of which is incorporated by reference herein in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

This disclosure is generally related to preventing and/or treating bleeding in a subject. More specifically, this disclosure is related to apparatuses (devices, systems, and methods) for preventing and/or treating bleeding in a patient through stimulation of the spleen.

BACKGROUND

Bleeding and blood loss can occur due to any of a number of causes such as traumatic injury from accidents or from surgery. For example, there are approximately 100,000,000 surgeries performed annually in the United States, with millions more worldwide (CDC, National Center for Health Statistics), with an associated inherent risk of bleeding, from minor to potentially life threatening. Aside from administration of tranexamic acid for select orthopedic procedures, there are no prophylactic systemic therapies available to administer to help improve hemostasis and minimize surgical bleeding.

Trauma is the third leading cause of death in the United States (CDC, National Center for Health Statistics). A common cause of death following traumatic injury is uncontrolled bleeding (CDC, National Center for Health Statistics). While modern tourniquets are sometimes available to help staunch hemorrhage following extremity trauma, these injuries are still dangerous. Approaches to control non-compressible torso hemorrhage remain even more limited and this is a common cause of death of U.S. soldiers on the battlefield.

Postpartum hemorrhage (PPH) is the leading cause of maternal deaths worldwide. The most common cause is poor contraction of the uterus. Other causes include uterine tears, retained placenta, and inadequate blood clotting. In the United States, approximately 11% of maternal deaths result from PPH, whereas in the developing world approximately 60% of maternal deaths result from PPH. This equates to 100,000 to 140,000 deaths per year. Existing treatments include medications such as oxytocin, misoprostol, and ergotamine, intravenous fluids, blood transfusions, and uterine massage. Surgery to repair cervical or vaginal lacerations or uterine rupture is sometimes necessary as well. Many of these therapeutic options are risky or unavailable in resource-poor areas, resulting in dramatically higher mortality rates.

Hemophilia A is an X-linked recessive disorder associated with spontaneous and prolonged bleeding episodes secondary to deficiencies in clotting factor VIII. More than 20,000 individuals in the United States suffer from this life-long disease. Up to 30% of children with severe hemophilia cannot receive standard factor VIII concentrates due to the development of inhibitor antibodies. Maintaining hemostasis then requires bypassing agents, such as activated prothrombin complex concentrate and recombinant factor VIIa, to help generate clot via alternative pathways. These costly therapies are associated with serious systemic thrombotic side effects, including myocardial ischemia, deep venous thrombosis, and pulmonary embolism. Thus, there is a need for new devices, methods, and systems to prevent and treat bleeding problems.

Described herein are devices, methods, and systems that address these issues and others related to blood loss and bleeding.

SUMMARY OF THE DISCLOSURE

The present invention represents a novel method and apparatus to reduce bleeding in a patient. More specifically, this disclosure is related to apparatuses (devices, systems) and methods for controlling bleeding and bleeding time in a patient through mechanical stimulation, such as through acoustic stimulation of the spleen. The apparatus may provide non-invasive stimulation of the spleen. Controlling bleeding may include preventing and/or treating bleeding (e.g., surgical bleeding, traumatic bleeding, bleeding related to other medical procedures or conditions, and inherited or acquired bleeding disorders).

Mechanistically, ultrasound stimulation may represent an alternative, non-invasive method to directly activating the cervical vagus nerve by activating the spleen and previously described Neural Tourniquet. Advantages of this method over pharmacological approaches include potentially higher specificity, fewer side effects, lower costs, and improved compliance. Advantages over implantable pulse generators for chronic nerve stimulation applications include avoidance of surgery and associated complications, both for the initial procedure and subsequent procedures for battery changes, and lower costs.

For example, described herein are methods of reducing bleeding (e.g., bleed time) in a subject, the method comprising: applying ultrasound stimulation to the subject's spleen; and reducing bleeding by at least 20%. The methods may include applying the ultrasound stimulation at an ultrasound stimulation frequency ranging from, e.g., 0.25 to 5.0 MHz for a predetermined duration (e.g., from 30 seconds to 5 minutes) to the subject's spleen. The ultrasound stimulation may be applied using a prescribed range of input voltage amplitudes (e.g., from 50 to 350 mVpp). In some examples, the ultrasound stimulation includes applying a focused ultrasound stimulation to the subject's spleen. The ultrasound stimulation may be applied transdermally/transcutaneously. Alternatively or additionally, in some examples the ultrasound may be applied invasively (e.g., during a surgical procedure) and/or via an implant. The ultrasound stimulation may be directed and/or focused at a center region of the subject's spleen and/or a hilum of the subject's spleen. The ultrasound stimulation may be applied without directly stimulating the vagus nerve and/or the trigeminal nerve. In some examples, the ultrasonic stimulation of the spleen is applied in combination with electrical or mechanical stimulation of the vagus nerve and/or the trigeminal nerve to reduce bleeding. In some examples, applying the ultrasound stimulation to the subject's spleen includes stimulating the splenic nerve. The bleed rate of the subject may be measured before, during and/or after applying the ultrasound stimulation to the subject's spleen.

In general, the subjects described herein may be referred to as patients or as patients in need of bleeding control; these subjects may include (but are not limited to) human subjects. The subject may be a non-human (e.g., animals, including domesticated animals).

Also described herein are methods of treating a bleeding subject that include determining when the subject is bleeding and applying ultrasound stimulation to the subject's spleen (e.g., using a frequency ranging from 0.25 to 5.0 MHz for a duration ranging from 30 seconds to 5 minutes to the subject's spleen).

Also described herein are methods of reducing bleeding time in a subject undergoing a surgery that include: applying ultrasound stimulation to the subject's spleen during the surgery or within 2 hours of performing the surgery on the subject; wherein the ultrasound stimulation comprises using an ultrasound frequency ranging from 0.25 to 5.0 MHz using an input voltage amplitude ranging from 50 to 350 mVpp for a duration ranging from 30 seconds to 5 minutes to the subject's spleen.

In any of these methods, the subject may be human or non-human.

As mentioned, any of these methods may include reducing bleeding time. For example, reducing bleeding time may comprises reducing bleeding time from of one or more of an internal hemorrhage or an external hemorrhage. Bleeding time may be reduced (e.g., the application of acoustic energy may be applied until the bleeding time is reduced) by more than 10%, 15%, 20%, 25%, 30%, 35%, 40%, 45%, 50%, 55%, 60%, 65%, 70%, etc. compared to untreated patients.

The apparatuses described herein are generally configured to perform any of these methods. For example, described herein are systems for reducing bleeding in a subject. The system may include: an ultrasound applicator comprising one or more ultrasound transmitters and a housing (e.g., a housing substrate) configured to applying ultrasound stimulation to the subject's spleen; and a controller coupled to the ultrasound applicator, the controller configured to deliver ultrasound stimulation from the one or more ultrasound transmitters at a frequency of between 0.25 to 5.0 MHz for a duration ranging from 30 seconds to 5 minutes to the subject's spleen to reduce bleed time in the patient by at least 20%.

The ultrasound applicator may include a housing configured to be secured to the subject's abdomen over the subject's spleen. The ultrasound applicator may comprise an array of ultrasound transmitters. In some examples, the ultrasound transmitters are configured to project ultrasound stimulation between 1 cm and 10 cm into the body. The ultrasound applicator may comprise one or more sensors, further wherein the controller is configured to detect an intercostal space and to select one or of the ultrasound transmitters of the ultrasound applicator overlaying the intercostal space. For example, the one or more sensors may comprise ultrasound sensors.

The housing may be a substrate that is flexible. For example, the housing may comprise a flexible substrate onto or into which the one or more ultrasound transmitters are secured.

In any of these systems, the controller may be configured to apply an input voltage amplitude ranging from 50 to 350 mVpp to drive eh application of the ultrasound from the ultrasound applicator.

The housing may comprise an adhesive pad adapted to be applied to the subject's abdomen over the subject's spleen. In some examples, the ultrasound applicator is coupled to the controller by a cord; alternatively, in some examples, the controller is enclosed within the housing of the ultrasound applicator and/or is attached to the housing (e.g., within a secondary housing) on the housing of the applicator.

These and other features and advantages are described herein.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative examples, in which the principles of the invention are utilized, and the accompanying drawings of which:

DETAILED DESCRIPTION

Figure 1A:
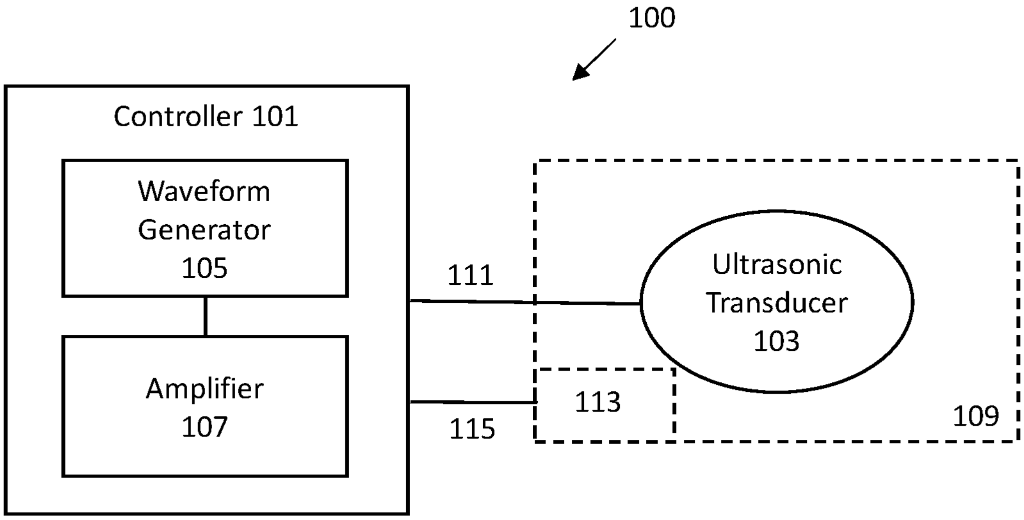
FIG. 1A is a schematic illustration of an example ultrasound apparatus for applying stimulation to a spleen to reduce bleeding.

The present invention relates to controlling (e.g., treating and/or preventing) bleeding in a patient by stimulation of the patient's spleen. More specifically, described herein are apparatuses (devices, systems, and methods) for controlling bleeding by applying mechanical stimulation, such as acoustic (e.g., ultrasound) stimulation, to reduce bleeding time, which is associate with a corresponding reduction of bleeding volume (blood loss). The spleen may be stimulated transdermally, and can therefore be noninvasive. Controlling bleeding may include preventing and/or treating bleeding such as surgical bleeding, traumatic bleeding, bleeding related to childbirth, bleeding related to other medical procedures or conditions, bleeding mediated or increased by anticoagulants, inherited or acquired bleeding disorders such as hemophilia, and for treating other forms and causes of bleeding.

As used herein, "treatment" includes prophylactic and therapeutic treatment. "Prophylactic treatment" refers to treatment before the onset of a condition (e.g., bleeding, an inflammatory condition, etc.) is present, to prevent, inhibit or reduce its occurrence.

As used herein, a patient or subject may be any animal, preferably a mammal, including a human, but can also be a companion animal (e.g., a cat or dog), a farm animal (e.g., a cow, a goat, a horse, a sheep) or a laboratory animal (e.g., a guinea pig, a mouse, a rat), or any other animal, preferably a mammal that has a spleen.

"Bleeding time" or "bleed time" as used herein refers to the length of time it takes to for bleeding to stop. In general, bleeding time may be controlled or influenced by how well blood platelets work to form a platelet plug. In an untreated subject, bleeding time is generally increased by the administration of anticoagulant, such as aspirin, heparin, and warfarin.

As used herein, the terms "reduce" or "reducing" when referring to bleeding (e.g., bleeding time) encompass at least a small but measurable reduction in bleeding over non-treated controls. Bleed time reduction may range from about 5% to about 70%. The bleed time may be reduced by at least any of the aforementioned percentages. For example, the bleed time may be reduced by at least 5%, at least 10%, at least 20%, at least 25%, at least 30%, at least 35%, at least 40%, at least 50%, at least 60%, at least 65%, at least 70%, or more than 70%. For example, a value between these ranges may be chosen so as to use a protocol or apparatus configured to reduce bleeding while minimizing side effects due to applied spleen stimulation. For instance, in some examples, the bleed time may be reduced by 5% to 70%, 10% to 50%, 20% to 60%, 30% to 70%, 40% to 70%, or 25% to 65%.

Spleen stimulation as described herein may be non-invasive. Mechanical stimulation may be, for example, transcutaneous (without breaching the skin). As used herein, non-invasive stimulation can be achieved, for example, by application of pressure and/or vibration means applied externally to the subject. The mechanical stimulation may be by means of sonic vibrator, such as ultrasound stimulation apparatus, applied to the surface of the subject's skin over, near and/or toward the patient's spleen. In some examples non-invasive sonic stimulation may be applied to the spleen. For example, electrical stimulation may be applied through the skin (transdermally) from one or more locations.

Splenic stimulation may directly or indirectly apply mechanical energy to one or more nerves or nerve plexuses. For example, ultrasound stimulation of the spleen may additionally stimulate the splenic nerve (splenic plexus). Whether an endogenous pathway for controlling (accelerating) clot formation (blood coagulation) is present at the spleen or at the splenic nerve, once activation of such a pro-coagulatory pathway is achieved by vibration/sonic stimulation, hemostasis is improved via accelerated clot formation specifically at the site of tissue injury. This may lead to less blood loss and a shorter duration of bleeding following tissue trauma with hemorrhage.

In some cases, mechanical splenic stimulation may also activate other physiological pathways, such as an anti-inflammatory pathway (e.g., cholinergic anti-inflammatory pathway). However, the conditions for targeting activation of the blood coagulation pathway may differ from those for targeting activation the anti-inflammatory pathway. For example, optimized parameters for ultrasound stimulation of the spleen for activating the anti-inflammatory pathway might not efficiently activate blood coagulation for achieving a reduced bleed time within a minimum threshold value. This minimum threshold of reduced bleed time may vary depending on the condition being treated. For example, bleed time reduction requirements for treating inherited or acquired bleeding disorders may differ from those for treating/preventing surgical bleeding. In some examples, the minimum threshold value of bleed time reduction as compared to an untreated subject is at least 10%, at least 20%, at least 30%, at least 40%, at least 50%, at least 60%, or at least 70%. For some conditions, it is desirable to reduce bleeding only to a certain extent. In such cases, there can be a maximum threshold value of reduced bleed time. In some examples, the maximum threshold of reduced bleed time as compared to an untreated subject is at most 10%, at most 20%, at most 30%, at most 40%, at most 50%, at most 60%, or at most 70%. In some cases, the bleed time reduction may range between any of the aforementioned values (e.g., from 10% to 70%, from 20% to 70%, from 40% to 60%, from 50% to 70%, from 50% to 60%, etc.).

Any of the splenic stimulation methods described herein can be implemented by applying acoustic energy to the spleen. In some examples, the acoustic energy is applied in pulsed waves. In some examples, the acoustic energy is applied continuously. In other examples, a combination of pulsed waves and continuous application of acoustic energy is used. In some examples, the acoustic energy is applied from a single ultrasound emitter. In other examples, the acoustic energy is applied from an array of ultrasound emitters in combination. The methods may involve focused ultrasound (FUS) techniques, where acoustic energy is focused using acoustic lenses to focus the acoustic energy to a target tissue. In some examples, high-intensity focused ultrasound (HIFU) techniques are used.

In general, the splenic stimulation described herein may be sufficient to result in a reduction in blood loss by the patient. Thus, the acoustic stimulation may be applied without simultaneous application of other therapies for blood loss. For example, the splenic stimulation may be applied without simultaneous pharmacological therapy. The acoustic stimulation may be applied without direct electrical stimulation of the vagus nerve and/or the trigeminal nerve. Direct electrical nerve stimulation may refer to stimulation provided by one or more electrodes (e.g., nerve cuff) in physical contact with the vagus nerve and/or the trigeminal nerve. The acoustic stimulation may be applied without indirect electrical stimulation of the vagus nerve and/or the trigeminal nerve. Indirect electrical nerve stimulation may refer to stimulation provided by one or more electrodes that are not in physical contact with the vagus nerve and/or the trigeminal nerve, such as by transcutaneous electrical stimulation. The acoustic stimulation may be applied without direct or indirect mechanical stimulation of the vagus nerve and/or the trigeminal nerve, such as by transcutaneous oscillating mechanical force and/or pressure (e.g., sonic or ultrasonic vibration) to the vagus nerve and/or the trigeminal nerve.

In general the splenic stimulation approaches described herein may be safer than traditional therapies. In general, an approach described herein may be more efficacious, safer, and less costly than traditional pharmacological therapies. For example, compared to pharmacological therapies, a non-invasive stimulation approach may provide higher specificity, fewer side effects, lower costs, and improved patient compliance. Compared to invasive (e.g., surgical)

approaches, the non-invasive stimulation avoids complications associated with such invasive treatments.

Although effective splenic stimulation to reduce blood loss may be applied without other therapies, in some examples, acoustic splenic stimulation may be used in conjunction with one or more other types of blood loss reduction treatments. For example, in some examples the sonic stimulation therapies described herein may be used in conjunction with vagus nerve and/or trigeminal nerve stimulation (e.g., electrical and/or mechanical stimulation) for the purpose of reducing bleeding. Examples of suitable nerve stimulation approaches for reducing blood loss are described in U.S. Pat. No. 8,729,129 and U.S. patent application Ser. No. 16/391,155, each of which is incorporated by reference herein in its entirety.

The methods for controlling bleeding described herein may be performed by any appropriate apparatus, including an ultrasound apparatus useful for stimulating the spleen. Preliminary work has suggested that a modified version of an ultrasound apparatus including a focused ultrasound therapy transducer, such as the Sonic Concept H106 ultrasound transducer (manufactured by Sonic Concepts, Inc. based in Bothell, Washington, USA). The ultrasound transducer may be connected to a power amplifier and a waveform generator, such as the Keysight Technologies™ 33120A waveform generator (manufactured by Keysight Technologies based in Santa Rosa, California, USA), to deliver non-invasive focused ultrasound stimulation to the spleen.

FIG. 1A is a schematic of a generic ultrasound stimulation apparatus 100 to treat bleeding. In this example, the apparatus generally includes an applicator 109 with at least one ultrasound transducers 103 for applying ultrasound stimulation to the spleen, which is connected to a controller 101 for controlling aspects of the ultrasound stimulation. The one or more transducers may be high-intensity focused ultrasound transducers. The controller includes a waveform generator 105 and optionally a power amplifier 107 for generating electronic signals to the transducer. The controller may include one or more processors to control aspects of stimulation such as the focal length, power and duration of the applied sonic stimulus. The controller may be a dedicated computing device for applying the ultrasound stimulation. In some examples, the controller is a tablet, phone, laptop, watch or other computing device. The power amplifier and waveform generator may be separate units or part of the same unit (e.g., enclosed within a single enclosure).

The ultrasound transducer may be, or be part of, a probe for direct or indirect application to the skin of the patient. In some examples the amplifier, waveform generator may be integrated with the probe. An ultrasound lotion or gel may be used to assist transmission of the ultrasound waves. In some examples, the probe is, or is part of, a handheld unit. In some cases, the probe includes a securement device to secure the probe/transducer to the patient's body. For example, the probe/transducer may be secured to the patient using a strap, belt and/or adhesive. In some cases, the probe/transducer may be integrated into a clothing or accessory worn by the subject. In some cases, the probe/transducer is part of a surgical device for treating or controlling bleeding before, during and/or after surgery.

In examples where the ultrasound transducer is a focused ultrasound transducer (FUS), the transducer may include an acoustic lens so that it emits a focused ultrasound beam having a corresponding focal zone (e.g., focal point) and focal length. The probe may be positioned such that the spleen is within the focal zone/focal length of the transducer.

Figure 1B:
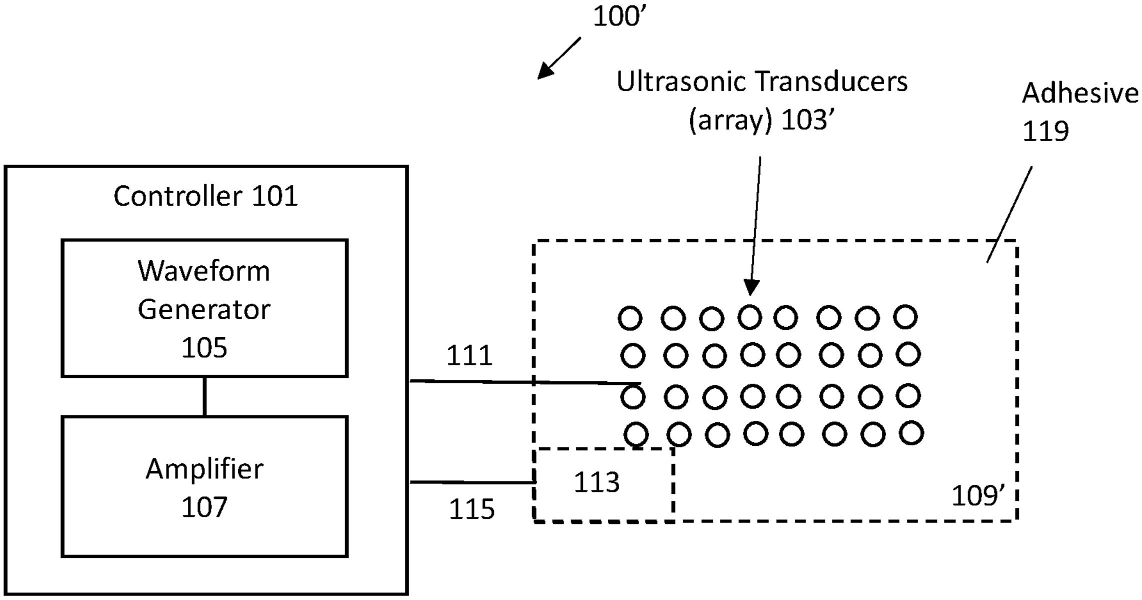
FIG. 1B is another example of a schematic illustration of an ultrasound apparatus for applying stimulation to a spleen to reduce bleeding.

FIG. 1B shows another example of an ultrasound stimulation apparatus to treat bleeding. In this example, the apparatus 100' includes an array of ultrasound transducers 103' for applying ultrasound stimulation to the spleen. The transducer array is part of an applicator 109' that may be configured to be applied to a patient's torso over the upper ribcage (e.g., over the spleen). For example, the applicator may include a housing that is configured to fit onto the patient's torso. In some examples, the housing may be a flexible substrate to which the one or more ultrasound transducers are attached. In some examples the applicator includes an adhesive and/or a hydrogel material 119 that may help secure it to the patient's skin and make a connection between the skin and the ultrasound transducer(s). The applicator may be single-use (e.g., disposable) or reusable. In some example the applicator includes a removable skin-contacting portion that can be replaced onto a reusable portion (include the one or more transducers). The one or more transducers may be high-intensity focused ultrasound transducers.

In FIG. 1B, the applicator is connected to a controller 101 for controlling aspects of the ultrasound stimulation. The controller may include a waveform generator 105 and optionally a power amplifier 107 for generating electronic signals to the transducer. The controller may include one or more processors for control aspects such as the focal length, power and duration of the applied sonic stimulus. The controller may be a dedicated computing device for applying the ultrasound stimulation. In some examples, the controller is a tablet, phone, laptop, watch or other computing device. The power amplifier and waveform generator may be separate units or part of the same unit (e.g., enclosed within a single enclosure).

In any of these apparatuses (e.g., systems, devices, etc.) the apparatus may be configured to apply ultrasound energy to the spleen by identifying an intercostal region (between two or more ribs, such as in particular, between the $9^{th}$ and $10^{th}$ or between the $10^{th}$ and $11^{th}$ ribs of the patient to whom the applicator has been applied. The apparatus may automatically identify the intercostal region and may be configured to apply energy from a subset of an array of the ultrasound transducers that are over the intercostal region for applying energy to the spleen, as described herein. Thus, and of these apparatuses may include one or more intercostal sensors for detecting the intercostal region. In some examples, the same ultrasound transducers used to apply the energy to the body may be used to detect the intercostal space between the ribs. For example, the controller may be configured to apply a sequence of sounding ultrasound pulses and to detect a return ultrasound signal to identify ribs underlying the applicator. The controller may then determine which ultrasound transducers are over an intercostal space and/or likely to be over the spleen and may select this subset of one or more ultrasound transducers to apply energy as described herein.

In some examples the controller unit may be directly connected to the transducer via one or more conductors 111. Alternatively, the controller may be within the housing of the applicator and may be coupled to or integral with the housing (see, e.g., FIG. 2D, below). Any of the apparatuses described herein may include one or more inputs, including user (physician, caregiver, nurse, self/patient, etc.) controls. Any of these apparatuses may also or alternatively include one or more sensors 113 for detecting a condition of the patient, which can be connected 115 (wired and/or wirelessly) to the controller 101 or to one or more other computing devices. The sensors may detect one or more physiological conditions of the subject, such as one or more of: blood loss/bleeding, blood pressure, heart rate, etc. The sensor data may be used to control the apparatus in a feedback loop. For example, one or more sensors may be used to modify (e.g., automatically and/or manually) the parameters of the ultrasound stimulation. In some cases, this is done in real time.

The ultrasonic devices described herein can be integrated into a surgical device configured to be positioned and/or secured to a subject about to undergo a surgery. The ultrasound treatment may be applied ahead of a scheduled surgery (e.g., 5 minutes ahead, 10 minutes ahead, 15 minutes ahead, 20 minutes ahead, 30 minutes ahead, or more) either continuously or discretely, and/or to reduce or control bleeding during and/or after the surgery. In some examples, these methods may be used to treat a patient following a surgery and/or following delivery of a baby (e.g., to reduce bleeding due to postpartum hemorrhage or any other medical procedure in which bleeding may be a concern (e.g., joint replacement or spine surgery).

In addition to acute bleeding, the methods and apparatuses described herein may be used to treat chronic bleeding. For example, any of these methods and apparatuses for reducing bleeding by splenic stimulation may be used to treat a subject having hemophilia. Hemophiliac subjects may be at risk for bleeding over their entire lives. The patient suffering from chronic bleeding may be treated with ultrasound stimulation at prescribed intervals, for example, one or more times a day, week, or month. In some cases, the device is portable such that the patient may keep the device at hand for applying ultrasound stimulation when there is a risk of bleeding. Alternatively, the patient may use a wearable unit (e.g., belt, band, etc.) to secure the ultrasound transducer to the patient or to apply the ultrasonic stimulation.

Figure 2A:
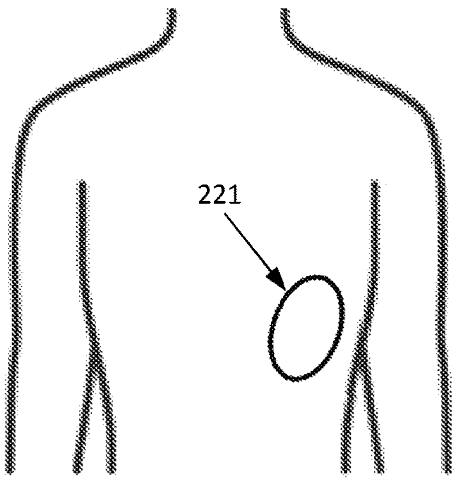
FIGS. 2A and 2B are schematic illustrations showing the location and structure of the spleen.

The method and apparatuses described herein may be configured to treat bleeding by applying stimulation to one or more regions of the spleen. FIG. 2A shows a schematic illustration of the general location 221 of the spleen. The spleen is generally in the upper left abdomen under the left part of the diaphragm. The spleen is generally at least partially behind the rib cage, for example, underneath the ninth, tenth and eleventh ribs. To apply sonic energy to the spleen, the transducer/applicator is typically placed on the left back and/or side of the patient's torso such that the head of the transducer is directed toward the spleen. In other cases, the transducer/applicator is placed at the left front upper torso at or near the lower ribs. The transducer/applicator maybe positioned at an angle relative to a surface of the skin to avoid or reduce interference from the rib(s). In some cases, the surface of the head of the transducer is angled between about 5 degrees and about 90 degrees (e.g., about 5°, 10°, 15°, 20°, 25°, 30°, 35°, 40°, 45°, 50°, 55°, 60°, 65°, 70°, 75°, 80°, 85°, or 90°) with respect to the skin surface.

Figure 2B:
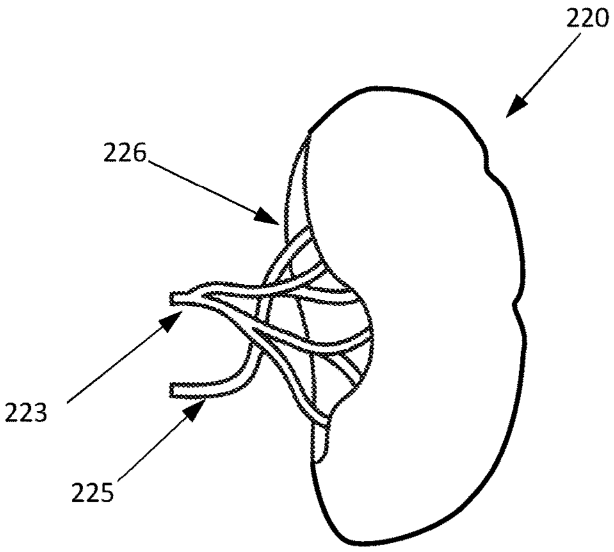

According to some examples, the transducer/applicator is placed such that a central region of the spleen is stimulated. FIG. 2B shows an illustration of the general anatomy of the spleen 220. The hilum 226 corresponds to a long fissure near the middle of the spleen and is the point of attachment for the gastrosplenic ligament and includes the point of insertion of the splenic artery 223 and splenic vein 225. In some examples, the ultrasound energy is focused at or near the central region of the spleen, including at least a portion of the hilum. For example, the surface of the head of the transducer may be pointed toward the central region of the spleen at or near the hilum, with the focal zone (focal length) of the focused ultrasound transducer adjusted to include the central region of the spleen at or near the hilum.

Figure 2C:
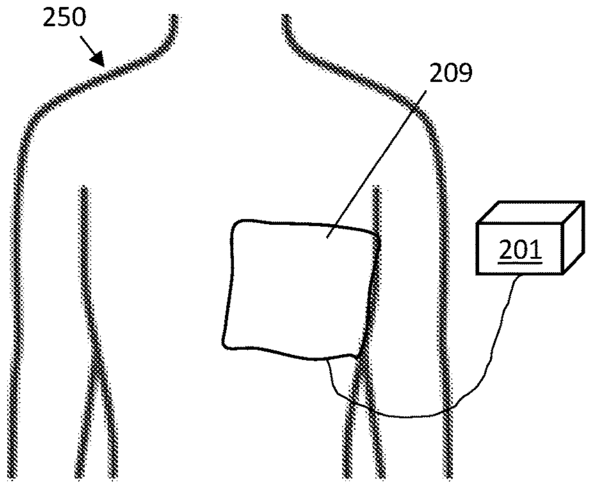
FIGS. 2C and 2D illustrate examples of apparatuses as described herein applied to a patient's body over the spleen.
Figure 2D:
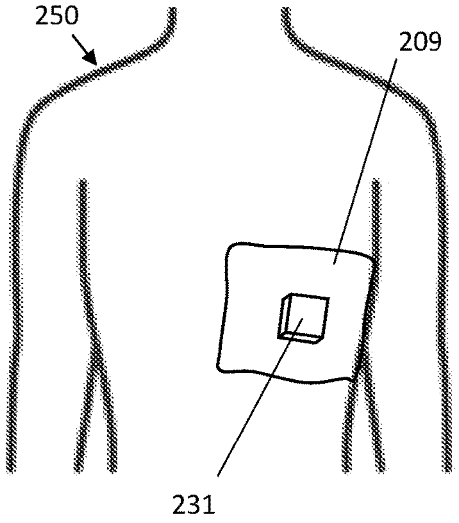

FIG. 2C illustrates one example of an apparatus as described herein applied to a patient 250. In FIG. 2C, an applicator 209 is shown applied to the patient 250. The applicator may be adhesively attached, e.g., by an adhesive and/or ultrasound-conductive gel (e.g., hydrogel) on the applicator. The applicator is attached over the region of the torso above the spleen. In this example, the applicator is coupled to a controller 201 that drives the ultrasound energy and/or may determine which ultrasound transducer to use to apply energy to the spleen. In FIG. 2D the applicator 209 includes a secondary housing 231 that encloses the controller, which is integrated into or with the applicator. In any of these examples the applicator may be said to include a housing. The housing may be rigid or flexible. For example, the housing may be a fabric material. The housing may also be referred to as a substrate. In general, this housing (or housing substrate) may support the one or more transducers and may be applied to the patient's torso over the spleen. In some examples the housing is configured, e.g., by including a curved or pre-curved surface to fit over a subject's upper torso above the spleen.

When acoustic energy is applied to stimulate the spleen to control bleeding, the acoustic energy may be applied within effective parameters ranges (intensity, frequency and/or duration ranges) for achieving at least a minimum threshold reduction of bleed time and/or at most a maximum threshold reduction of bleed time, as described herein. In some examples, the ultrasound (e.g., FUS) frequency ranges from about 0.25 to 10.0 MHz (e.g., from about 0.25 to 5.0 MHz, from about 0.25 to 2.5 MHz, from about 0.1 to 2 MHz, from about 0.25 to 1.5 MHz, etc.). In some examples, the frequency is constant. In some examples, the frequency may be varied by, e.g., −/+5%, 10%, 15%, 20%, 25%, 30%, 35%, 50%, etc.

The ultrasound (e.g., FUS) intensity as measured by the input voltage amplitude (mVpp) may range from about 50 to 400 mVpp (e.g., from about 100 to 300 mVpp, from about 50 to 350 mVpp, from about 10 to 250 mVpp, from about 10 to 200 mVpp, etc.). In some examples, the input voltage amplitude is no more than 400 mVpp (e.g., no more than 350 mVpp, no more than 350 mVpp, no more than 300 mVpp, no more than 250 mVpp, no more than 200 mVpp, no more than 150 mVpp, no more than 100 mVpp, etc.). The input waveform of the ultrasound (e.g., FUS) stimulation may be characterized as having any of a number of waveform shapes, such as sinusoidal, square, triangle, sawtooth, etc.

The duty cycle of an ultrasound (e.g., FUS) treatment (within an "on time" of stimulation) may range from about 10 to 500 cycles/burst (e.g., from about 50 to 300 cycles/burst, from about 100 to 300 cycles/burst, from about 100 to 200 cycles/burst, etc.). The ultrasound (e.g., FUS) burst duration may range from about 50 microseconds (μsec) to 10 milliseconds (ms) (e.g., from about 100 μsec to 5 ms, from about 500 μsec to 2 ms, from about 100 μsec to 2 ms, from about 200 μsec to 10 ms, etc.).

In any of the ultrasound (e.g., FUS) stimulation treatments described herein, a total treatment duration may range from about 30 seconds (sec) to 2 hours (hrs) (e.g., from about 30 sec to 5 minutes (min), from about 1 min to 10 min, from about 1 min to 5 min, from about 30 sec to 5 min, from about 1 min to 30 min, from about 30 sec to 5 min, from about 30 sec to 1 hr, etc.). In some examples, the stimulation may be applied for longer than 1 hour. In some examples, the stimulation may be applied until a reduction in bleeding is detected or the apparatus is manually shut off. There may be an "off time" or delay (e.g., rest interval) between rounds of stimulation. For example, the off-time or delay may range from about 1 sec to 30 minutes (e.g., from about 30 sec to 1 min, from about 15 sec to 5 min, from about 30 sec to 2 min, from about 30 sec to 10 min, etc.).

The apparatuses and methods described herein may be suitable for therapeutically or prophylactically treating subjects suffering from or at risk from suffering from unwanted bleeding from any cause such as: bleeding disorders including but not limited to afibrinogenemia, Factor II deficiency, Factor VII deficiency, fibrin stabilizing factor deficiency, Hageman Factor deficiency, hemophilia A, hemophilia B, hereditary platelet function disorders (e.g., Alport syndrome, Bernard-Soulier Syndrome, Glanzmann thromblasthenia, gray platelet syndrome, May-Hegglin anomaly, Scott syndrome, and Wiskott-Aldrich syndrome), parahemophilia, Stuart Power Factor deficiency, von Willebrand disease, thrombophilia, or acquired platelet disorders (such as those caused by common drugs: antibiotics, and anesthetics, blood thinners, and those caused by medical conditions such as: chronic kidney disease, heart bypass surgery, and leukemia), childbirth, injury, menstruation, and surgery. An unwanted bleeding treated using any of the apparatuses or methods described herein may include an internal hemorrhage or an external hemorrhage. An internal hemorrhage includes a hemorrhage in which blood is lost from the vascular system inside the body, such as into a body cavity or space. An external hemorrhage includes blood loss outside the body. In some cases, the methods and apparatuses are used to control acute bleeding from trauma, such as from traffic and other accidents, and/or from combat.

Figure 3:
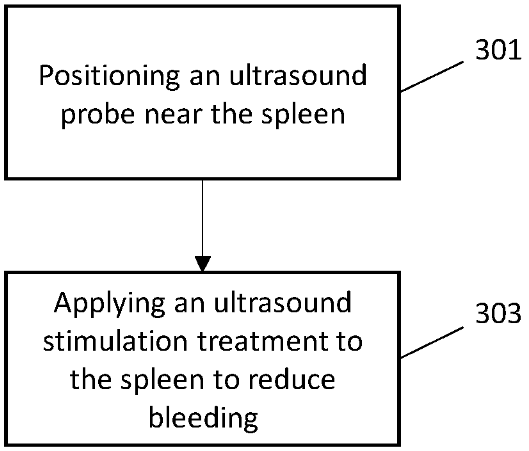
FIG. 3 is a flowchart showing an example method of reducing bleeding in a subject.

FIG. 3 shows a flowchart indicating an example method for controlling/reducing bleeding in a patient. A patient in need of reduced bleeding (e.g., experiencing acute bleeding or suffering from a bleeding disorder) may be treated by positioning an ultrasound probe on or near the subject's spleen (301). In some cases, a gel, lotion or other conductive medium is used between the probe and the patient's skin. The ultrasound probe may include a securing device to maintain a position of the probe relative to the spleen. For example, the securing device may position the probe at a predefined angle and/or distance with respect to the spleen. Positioning the ultrasound probe may include adjusting the angle/distance of the probe such that the spleen is within a focal zone/focal length of the ultrasound transducer. In some cases, one or more specified regions of the spleen, such as a central portion of the spleen and/or the hilum of the spleen, is within the focal zone/focal length of the ultrasound transducer.

Once properly positioned, an ultrasound stimulation treatment may be applied to the spleen (303). The treatment parameters may vary depending of the severity and/or the type of bleeding (e.g., acute or chronic). In some cases, the ultrasound treatment is adjusted until the patient's bleeding is reduced (or estimated to be reduced) by a predetermined amount. For example, the blood loss/bleeding may be measured after a certain period of treatment to determine whether the ultrasound treatment is effectively reducing the blood loss. The stimulation parameters (e.g., frequency, input voltage, etc.) may be adjusted based on the measurements until a desired bleed rate is achieved.

Examples

Figure 4A:
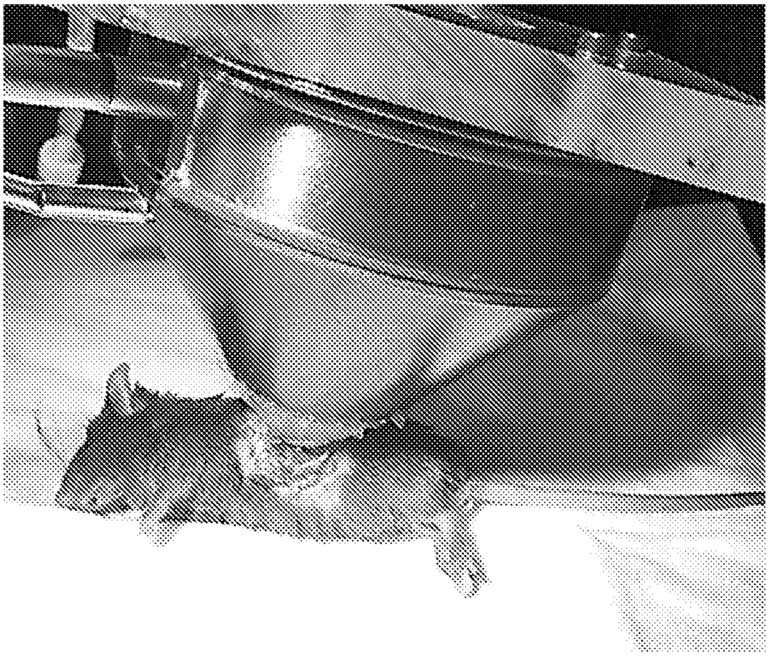
FIGS. 4A and 4B show example experimental setups for an ultrasound stimulation of the spleen of a mouse and a control ultrasound stimulation of the quadriceps muscle of a mouse.
Figure 4B:
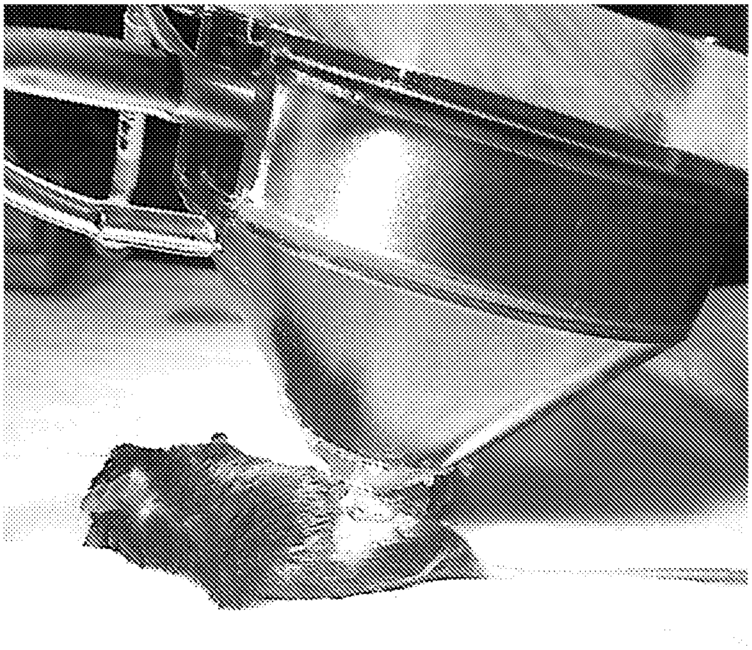

FIGS. 4A-4B illustrate an experimental set-up that was used to illustrate the application of ultrasound stimulation to the spleen of rodents to reduce bleeding, serving as an experimental model system predictive of the reduction of bleeding time by the application of ultrasound to the spleen in a human in need thereof. The animals used were adult male 8-12 week old C57BL/6J mice (20-25 g, Taconic) housed at 25° C. on a 12-hour light/dark cycle. Standard animal chow and water were freely available. All animal experiments were performed in accordance with the National Institutes of Health (NIH) Guidelines under protocols approved by the Institutional Animal Care and Use Committee of The Feinstein Institutes for Medical Research.

FIG. 4A shows a setup for ultrasound stimulation applied to a mouse's spleen. The animals were anesthetized with ketamine (144 mg/kg, i.p.) and xylazine (14 mg/kg, i.p.). The left side of the animal was shaved with animal clippers. After seven minutes, animals were placed in the right lateral decubitus position. The spleen was located by palpating the caudal border of the rib cage along the line drawn between the ventral aspect of the ear and the base of the tail. A spot was drawn on the animal's skin at the intersection of these two lines to aim the opening of a 1.1 MHz FUS transducer (Sonic Concepts, H106). The transducer was tilted 20 degrees cranially to avoid the ribs. Ultrasound gel was applied to the area. The transducer was connected to a 350 L RF power amplifier (Electronics & Innovations) and the signal was controlled by a 33120A function/waveform generator (Keysight Technologies). Function/waveform generator parameters were set to provide stimulation according to specified parameters (e.g., frequency, pulse amplitude, duration).

FIG. 4B shows a setup for a control ultrasound stimulation applied to a mouse's leg used as a control. The control-stimulated animals were anesthetized and placed in a left lateral decubitus position. The area of the lateral aspect of the right quadriceps was shaved with animal clippers. The transducer was placed on the line between the ventral aspect of the ear and the base of the tail in the middle of the muscle. The control animals underwent the same stimulation paradigm as experimental animals (FIG. 4A).

In a first set of experiments, the waveform generator parameters were set to 1.1 MHz sinusoidal wave, 200 mVpp, 0 offset, 150 cycles/burst, 500 microseconds (μsec) burst. Stimulation occurred for 60 seconds (sec) with a 30 sec rest interval and then another 60 sec stimulation. The waveform generator parameters were the same for both the experimental (FIG. 4A) and control-stimulated (FIG. 4B) animals.

Following focused ultrasound stimulation (FUS) in both the experimental and control-stimulated animals, tails were immersed in water at 37±1° C. for five minutes. Tails were then removed from the solution, 2 millimeters (mm) of tail were amputated with a razor blade, and immediately placed into a 50 mL beaker containing water at 37° C. Tails were allowed to bleed uncontrolled until bleeding stopped for a minimum of ten seconds. This duration of bleeding was recorded as bleeding time.

Figure 5:
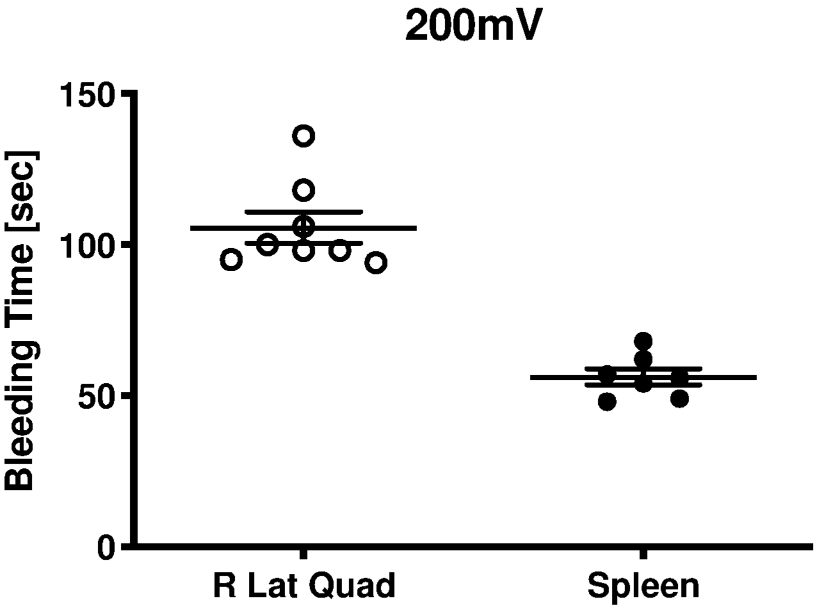
FIG. 5 is a graph showing bleeding times for mice after treatment with ultrasound stimulation to the spleen using parameters to reduce bleed times.

As shown in FIG. 5, high intensity FUS stimulation of the spleen significantly reduced bleeding time in a murine model of arterial tail injury and hemorrhage compared to control stimulation (quadriceps stimulation) using the same stimulation parameters. In particular, the spleen-stimulated animals had a bleed time of 56.3±2.7 sec versus the control-stimulated animals which had a bleed time of 105.6±5.1 sec (n=7-8/group, $p<0.0001$). In some cases, the ultrasound stimulator was placed under the left rib cage aimed cephalad, at an approximately 20 degree angle to the skin surface, and the probe was pushed into the skin for a depth of about 5-10 mm. Preliminary data from humans shows a similar targeting may be useful.

In humans, although the spleen may vary in size between individuals, a spleen is typically around 3-5.5 inches long (e.g., approximately 1 inch by 3 inches by 5 inches) and is positioned between the 9th and 11th ribs. The ultrasound stimulation described herein may be configured to apply the bulk of the ultrasound energy to the region of the spleen within the outer capsule, and in particular, the white pulp region or the nerves innervating the white pulp. In some examples, the ultrasound energy may target the white pulp primarily or exclusively. In some examples the ultrasound energy may target the red pulp (or the nerves innervating the red pulp). In some examples both the red pulp and white pulp regions may be targeted.

Figure 6A:
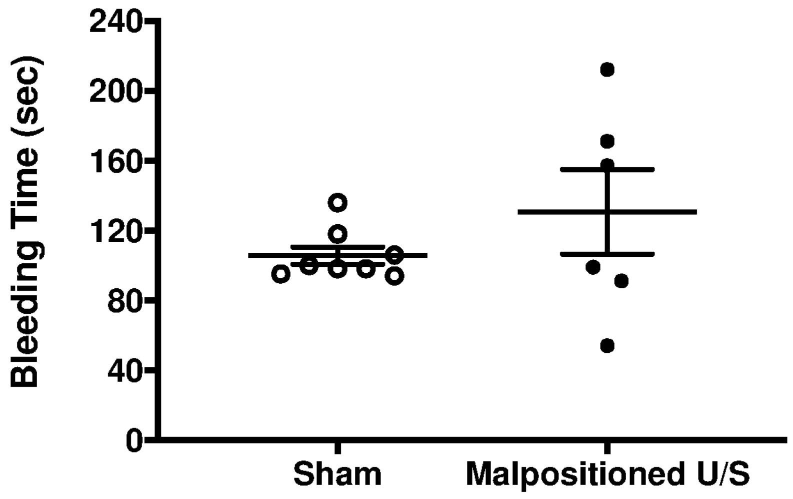
FIGS. 6A and 6B are graphs showing bleeding times for mice after treatment with a malpositioned ultrasound stimulation and using an inadequate input voltage.

In some cases, proper targeting, e.g., of the spleen (such as portion(s) of the spleen innervating the white pulp of the spleen) may result in an effective reduction in bleed time. In some examples the red pulp region may be targeted. Ultrasound energy applied to other regions outside of the spleen, or insufficiently targeting the white pulp region of the spleen may be less effective or ineffective. FIG. 6A show results of a second set of experiments, where ultrasound stimulation of wild-type C57BL/6J mice was used to illustrate the effects of positioning of the ultrasound stimulation probe. In this set of experiments, the same stimulation parameters (1.1 MHz sinusoidal wave, 200 mVpp, 0 offset, 150 cycles/burst, 500 microseconds (μsec) burst) were used to apply ultrasound stimulation to the mice. The same experimental setup was used to set up the control (quadriceps) stimulation described above (FIG. 4B). In these experiments, instead of properly positioning the ultrasound probe toward the center of the spleen, the ultrasound probe was positioned off center in relation to the spleen and splenic hilum (malpositioned U/S). The bleeding time was recorded after tail transection, as described above. In addition, necropsy was performed to determine the anatomic location of spleen in relation to skin surface marking of ultrasound probe. These results indicate that failure to adequately target the ultrasound probe (e.g., on the spleen, such as instead targeting the splenic hilum) does not adequately reduce bleeding time (control, labeled "sham" in FIG. 6A) 105.6 sec vs. malpositioned U/S 130.7 sec, p=0.26).

Figure 6B:
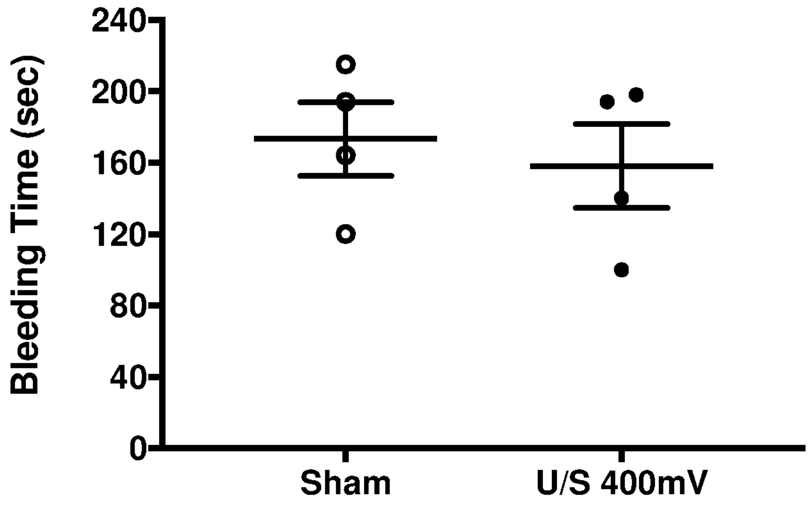

FIG. 6B show results of a third set of experiments, where ultrasound stimulation of wild-type C57BL/6J mice was used to illustrate the effects of input voltage to the ultrasound stimulation probe. In this set of experiments, the same stimulation parameters described above with reference to FIG. 4A (1.1 MHz sinusoidal wave, 0 offset, 150 cycles/burst, 500 microseconds (μsec) burst) were used to apply ultrasound stimulation to the mice except for input voltage. In particular, an input voltage of 400 mVpp (400 mV) was used instead of 200 mVpp. The bleeding time was recorded after tail transection, as described above. The results indicate that higher voltages are not more effective to adequately reduce bleeding time (200 mVpp, labeled "sham" in FIG. 6B) 173.3 sec vs. 400 mV U/S 158 sec, p=0.64). Thus, the applied ultrasound energy may have a saturation power level (e.g., input voltage), above which there is no further improvement in achieving consistent and significant reduction in bleed time.

Although the majority of examples provided herein describe non-invasive (e.g., transdermal) stimulation, any of these methods and apparatuses may be used for stimulation of the spleen during an open procedure (e.g., surgical procedure), e.g., to stimulate the spleen intraoperatively. For example, a device may be used intraoperatively to reduce bleeding during a medical procedure. In any of these methods and apparatuses, a physician (e.g., surgeon) may use ultrasound stimulation of the spleen to modify bleeding after trying other hemostatic methods (e.g., before the splenic stimulation). Furthermore, any of these methods or apparatuses may include implanting an ultrasound transducer at or near the spleen in order to provide ultrasound stimulation of the spleen.

As mentioned above, also described herein are systems for reducing bleed time (reducing time to clotting, etc.), as shown and described in FIG. 1A, above. Any of these systems may include software, hardware and/or firmware to control the applied power (e.g., voltage, frequency, etc.), dose timing, and/or targeting (confirming targeting of spleen, splenic region(s), etc.). The applicator (transducer) may be adapted to deliver the dose to the spleen and/or splenic sub-region. For example, the applicator may be configured to be positioned between the ribs (between $9^{th}$ and $10^{th}$ or $10^{th}$ and $11^{th}$) for targeting the spleen, etc. In some examples the applicator may be adhesively applied to the body for repeated stimulation. For example, the applicator may be placed on the subject's back over the spleen for dose delivery.

Preliminary data suggests that similar results from the mouse data shown above also apply to human subjects; specifically, ultrasound stimulation applied directly to the spleen results in a significant decrease in bleed time. The ultrasound may be applied for between 1 second and 10 minutes, and one or more treatments (e.g., two treatments, three treatments, four treatments, etc.) separated by between 1 minute and 12 hours (e.g., 1 minute and 8 hours, 1 minute and 4 hours, 1 minute and 2 hours, 1 minute and 1 hour, 10 minutes and 8 hours, 10 minutes and 4 hours, 10 minutes and 2 hours, 30 minutes and 12 hours, 30 minutes and 8 hours, 30 minutes and 4 hours, 1 hour and 12 hours, 1 hour and 8 hours, 1 hour and 4 hours, etc.) may be used to provide a significant reduction in bleeding, e.g., reducing the time to stop bleeding, such as reducing the time for clot formation at the location of hemorrhage.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one example, the features and elements so described or shown can apply to other examples. It will also be appreciated by those of skill in the art that references to a structure or feature that is disposed "adjacent" another feature may have portions that overlap or underlie the adjacent feature.

Terminology used herein is for the purpose of describing particular examples only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and examples such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative examples are described above, any of a number of changes may be made to various examples without departing from the scope of the invention as described by the claims. For example, the order in which various described method steps are performed may often be changed in alternative examples, and in other alternative examples one or more method steps may be skipped altogether. Optional features of various device and system examples may be included in some examples and not in others. Therefore, the foregoing description is provided primarily for exemplary purposes and should not be interpreted to limit the scope of the invention as it is set forth in the claims.

The examples and illustrations included herein show, by way of illustration and not of limitation, specific examples in which the subject matter may be practiced. As mentioned, other examples may be utilized and derived there from, such that structural and logical substitutions and changes may be made without departing from the scope of this disclosure. Such examples of the inventive subject matter may be referred to herein individually or collectively by the term "invention" merely for convenience and without intending to voluntarily limit the scope of this application to any single invention or inventive concept, if more than one is, in fact, disclosed. Thus, although specific examples have been illustrated and described herein, any arrangement calculated to achieve the same purpose may be substituted for the specific examples shown. This disclosure is intended to cover any and all adaptations or examples of various examples. Combinations of the above examples, and other examples not specifically described herein, will be apparent to those of skill in the art upon reviewing the above description.

What is claimed is:

1. A system for reducing blood loss in a subject, the system comprising:

an ultrasound applicator comprising one or more ultrasound transmitters and a housing configured to apply ultrasound stimulation to the subject's spleen, wherein the housing is configured to be secured to the subject's abdomen over the subject's spleen; and a controller coupled to the ultrasound applicator, the controller configured to deliver ultrasound stimulation from the one or more ultrasound transmitters at a frequency of between 0.25 to 5.0 MHz by applying an input voltage amplitude ranging from 50 to 350 mVpp to drive application of ultrasound from the ultrasound applicator for a duration ranging from 30 seconds to 5 minutes to the subject's spleen to target activation of the blood coagulation pathway and reduce bleed time in the subject by at least 20%.

2. The system of claim 1, wherein the ultrasound applicator comprises an array of ultrasound transmitters.

3. The system of claim 1, wherein the ultrasound transmitters are configured to project ultrasound stimulation between 1 cm and 10 cm into the subject's body.

4. The system of claim 1, wherein the ultrasound applicator comprises one or more sensors, further wherein the controller is configured to detect an intercostal space and to select one or more of the ultrasound transmitters of the ultrasound applicator overlaying the intercostal space.

5. The system of claim 1, wherein the housing comprises a flexible substrate onto which the one or more ultrasound transmitters are secured.

6. The system of claim 1, wherein the housing comprises an adhesive pad adapted to be applied to the subject's abdomen over the subject's spleen.

7. The system of claim 1, wherein the ultrasound applicator is coupled to the controller by an electrical conductor.

8. The system of claim 1, wherein the controller is enclosed within the housing of the ultrasound applicator.

9. A method of reducing blood loss in a subject, the method comprising:

applying ultrasound stimulation non-invasively to the subject's spleen from one or more ultrasound transmitters at a frequency of between 0.25 to 5.0 MHz by applying an input voltage amplitude ranging from 50 to 350 mVpp to drive application of ultrasound from an ultrasound applicator for a duration ranging from 30 seconds to 5 minutes; and reducing bleed time by at least 20%, wherein applying the ultrasound stimulation includes applying the ultrasound stimulation to the subject's spleen to target activation of the blood coagulation pathway without directly stimulating trigeminal nerve.

10. The method of claim 9, wherein applying the ultrasound stimulation includes applying a focused ultrasound stimulation to the subject's spleen.

11. The method of claim 9, wherein the ultrasound stimulation is applied transdermally.

12. The method of claim 9, wherein applying the ultrasound stimulation includes focusing the ultrasound stimulation at a center region of the subject's spleen.

13. The method of claim 9, wherein applying the ultrasound stimulation includes focusing the ultrasound stimulation at a hilum of the subject's spleen.

14. The method of claim 9, wherein applying the ultrasound stimulation includes applying the ultrasound stimulation to the subject's spleen without directly stimulating a vagus nerve.

15. The method of claim 9, wherein applying the ultrasound stimulation to the subject's spleen includes stimulating a splenic nerve.

16. The method of claim 9, further comprising measuring a bleed rate of the subject before, during or after applying the ultrasound stimulation to the subject's spleen.

17. A system for reducing blood loss in a subject, the system comprising:

an ultrasound applicator comprising one or more ultrasound transmitters and a housing configured to apply ultrasound stimulation to the subject's spleen, wherein the ultrasound applicator comprises one or more sensors, further wherein the controller is configured to detect an intercostal space and to select one or more of the ultrasound transmitters of the ultrasound applicator overlaying the intercostal space; and a controller coupled to the ultrasound applicator, the controller configured to deliver ultrasound stimulation from the one or more ultrasound transmitters at a frequency of between 0.25 to 5.0 MHz by applying an input voltage amplitude ranging from 50 to 350 mVpp to drive application of ultrasound from the ultrasound applicator for a duration ranging from 30 seconds to 5 minutes to the subject's spleen to target activation of the blood coagulation pathway and reduce bleed time in the subject by at least 20%.

18. The system of claim 17, wherein the one or more sensors comprise ultrasound sensors.

* * * * *